United States Patent
Nojiri et al.

(10) Patent No.: US 10,456,333 B2
(45) Date of Patent: Oct. 29, 2019

(54) DENTAL ADHESIVE

(71) Applicant: KURARAY NORITAKE DENTAL INC., Kurashiki-shi (JP)

(72) Inventors: Yamato Nojiri, Tainai (JP); Mitsuru Takei, Yokohama (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 15/781,745

(22) PCT Filed: Dec. 6, 2016

(86) PCT No.: PCT/JP2016/005071
§ 371 (c)(1),
(2) Date: Jun. 6, 2018

(87) PCT Pub. No.: WO2017/098724
PCT Pub. Date: Jun. 15, 2017

(65) Prior Publication Data
US 2018/0360696 A1 Dec. 20, 2018

(30) Foreign Application Priority Data
Dec. 7, 2015 (JP) .................. 2015-238788

(51) Int. Cl.
*A61K 6/083* (2006.01)
*A61K 6/087* (2006.01)
*A61K 6/00* (2006.01)
*C09J 133/10* (2006.01)
*C09J 133/26* (2006.01)

(52) U.S. Cl.
CPC ............... *A61K 6/087* (2013.01); *A61K 6/00* (2013.01); *A61K 6/0023* (2013.01); *C09J 133/10* (2013.01); *C09J 133/26* (2013.01); *A61K 6/083* (2013.01)

(58) Field of Classification Search
CPC .................................................. A61K 6/083
See application file for complete search history.

(56) References Cited

U.S. PATENT DOCUMENTS

| | | | |
|---|---|---|---|
| 4,719,297 A | 1/1988 | Henne et al. | |
| 5,300,537 A | 4/1994 | Mueller et al. | |
| 6,953,832 B2* | 10/2005 | Moszner | A61K 6/0017 106/35 |
| 9,844,495 B2* | 12/2017 | Kudo | A61K 6/00 |
| 10,123,947 B2* | 11/2018 | Takei | A61K 6/00 |
| 10,322,070 B2* | 6/2019 | Moszner | A61K 6/0023 |
| 2008/0103223 A1 | 5/2008 | Klee et al. | |
| 2017/0196778 A1 | 7/2017 | Nojiri et al. | |

FOREIGN PATENT DOCUMENTS

| | | |
|---|---|---|
| CA | 2368064 A1 | 7/2002 |
| EP | 0009348 B1 | 7/1983 |
| JP | 57-197289 A | 12/1982 |

(Continued)

OTHER PUBLICATIONS

International Search Report dated Feb. 28, 2017, in PCT/JP2016/005071, filed Dec. 6, 2016.

Moszner, N. et al., "Monomers for Adhesive Polymers, 4ª, Synthesis and Radical Polymerization of Hydrolytically Stable Crosslinking Monomers", Macromolecular Materials and Engineering, vol. 288, No. 8, 2003, pp. 621-628.

Demirgoez, D. et al., "Asymmetric Bihomologous Crosslinkers for Bicomponent Gels—The Way to Strongly Increased Elastic Moduli", Journal of Applied Polymer Science, vol. 115, No. 2, 2010, pp. 896-900.

*Primary Examiner* — Michael F Pepitone
(74) *Attorney, Agent, or Firm* — Oblon, McClelland, Maier & Neustadt, L.L.P.

(57) ABSTRACT

Provided herein is a self-etching dental adhesive that exhibits excellent adhesiveness not only to dentin untreated by phosphoric acid etching, but to dentin treated by phosphoric acid etching. The present invention relates to a dental adhesive containing a (meth)acrylamide compound (a), an asymmetric acrylamide-methacrylic acid ester compound (b), and an acid group-containing (meth)acrylic polymerizable monomer (c). The (meth)acrylamide compound (a) is at least one selected from the group consisting of compounds represented by general formula (1), and compounds represented by general formula (2). The asymmetric acrylamide-methacrylic acid ester compound (b) is a compound represented by general formula (3).

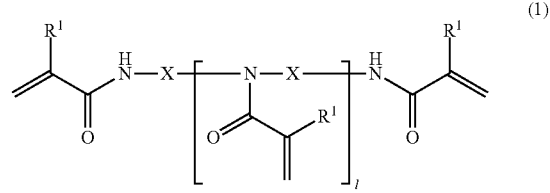

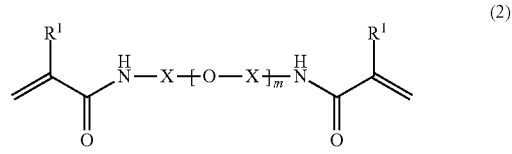

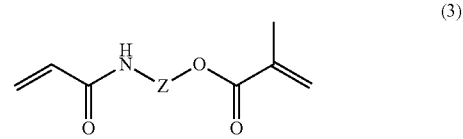

(In the formulae, the meanings of the symbols are omitted.)

11 Claims, No Drawings

(56) References Cited

FOREIGN PATENT DOCUMENTS

| | | |
|---|---|---|
| JP | 3-204846 A | 9/1991 |
| JP | 9-3109 A | 1/1997 |
| JP | 10-245525 A | 9/1998 |
| JP | 2000-159621 A | 6/2000 |
| JP | 2001-270856 A | 10/2001 |
| JP | 2002-212019 A | 7/2002 |
| JP | 2003-96122 A | 4/2003 |
| JP | 2009-542740 A | 12/2009 |
| JP | 2013-209341 A | 10/2013 |
| WO | WO 2015/190099 A1 | 12/2015 |

* cited by examiner

DENTAL ADHESIVE

TECHNICAL FIELD

The present invention relates to a dental adhesive containing a specific multifunctional (meth)acrylamide compound, and an asymmetric acrylamide-methacrylic acid ester compound. Specifically, the present invention relates to a dental adhesive used for bonding between tooth hard tissues (tooth structures) and dental restorative materials such as dental composite resins, dental compomers, and dental resin cements.

BACKGROUND ART

For restoration of tooth structures (enamel, dentin, and cementum) damaged, for example, by dental caries, restorative filling materials such as filling composite resins and filling compomers, or crown restoration materials such as metal alloys, porcelains, and resin materials, are typically used. In general, however, restorative filling materials and crown restoration materials (both of these materials may collectively be referred to as "dental restorative materials" in the present description) themselves have no adhesive properties to tooth structures. This is why bonding between tooth structures and dental restorative materials conventionally employs various adhesive systems involving the use of adhesives. An example of conventionally-employed adhesive systems is an adhesive system of the so-called acid etching-type (total etching-type), in which the surface of a tooth structure is subjected to an etching treatment using an acid etching material such as an aqueous phosphoric acid solution, and then a bonding material, which is an adhesive, is applied to the tooth structure so as to bond the tooth structure and a dental restorative material.

Adhesive systems of the so-called self-etching type, which involve no use of any acid etching material, have also been known. Self-etching adhesive systems that had been predominantly used in the past are two-step adhesive systems in which a self-etching primer containing an acidic monomer, a hydrophilic monomer, and water is applied to the surface of a tooth structure and then a bonding material containing a crosslinkable monomer and a polymerization initiator is applied directly to the primer without rinsing with water. In recent years, however, one-step adhesive systems using a one-part dental adhesive (one-part bonding material) having functions of both a self-etching primer and a bonding material have been widely used.

In some applications, the self-etching adhesive system employs a technique called selective etching, in which only the enamel is subjected to phosphoric acid etching as a pretreatment to improve adhesiveness for enamel, including when restoring portions that are highly dependent on enamel bonding, such as an occlusal surface of a molar, and a fractured central incisor, or when high adhesiveness is needed for the enamel. In selective etching, however, treating enamel also treats the dentin at the same time at the enamel-dentin boundaries. Phosphoric acid etching, which is usually highly demineralizing, is known to expose collagen fibers through demineralization of hydroxyapatite when applied to dentin, which contains organic material such as collagen. The collagen in the exposed dentin contracts during rinsing and drying, and prevents smooth penetration of the polymerizable monomer component contained in the dental adhesive. It has accordingly been difficult with a self-etching dental adhesive to provide high adhesiveness for dentin subjected to phosphoric acid etching, and there is a demand for a self-etching material having improved adhesiveness to dentin subjected to phosphoric acid etching.

In general, a one-part bonding material contains monomer components such as an acidic monomer, a hydrophilic monomer, and a crosslinkable monomer, and (meth)acrylate compounds are usually used as such monomer components.

One-part bonding materials are required to have high adhesiveness to tooth structures (in particular, enamel and dentin), and further improvement of these properties is required. In response to these requirements, use of a (meth) acrylamide compound, which is a monomer component less susceptible to hydrolysis than a (meth)acrylate compound, has been reported to provide a dental composition with improved storage stability and high adhesiveness to dentin and enamel (see, for example, Patent Literatures 1 to 3).

Patent Literature 1 proposes a one-part dental adhesive composition containing: an acidic monomer; a bifunctional (meth)acrylamide compound represented by the general formula (5) having two (meth)acrylamide groups both of which are secondary amide groups, or a bifunctional (meth) acrylamide compound represented by the general formula (6) having two (meth)acrylamide groups both of which are tertiary amide groups; a solvent (for example, water); and a curing agent (for example, polymerization initiator) (hereinafter, in the present description, a (meth)acrylamide compound having two (meth)acrylamide groups both of which are secondary amide groups, and a (meth)acrylamide compound having two (meth)acrylamide groups both of which are tertiary amide groups may be referred to as symmetric (meth)acrylamide compounds, for the sake of convenience).

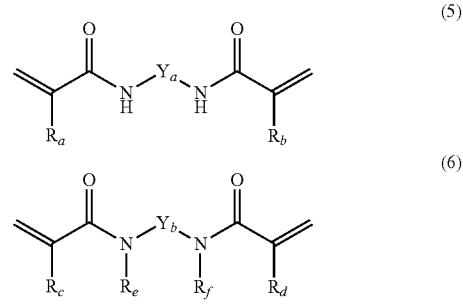

wherein $R_a$, $R_b$, $R_c$, and $R_d$ are each independently a hydrogen atom or a methyl group, $R_e$ and $R_f$ are each independently a group such as an alkyl group and an aryl group ($R_e$ and $R_f$ do not represent a hydrogen atom), and $Y_a$ and $Y_b$ are each independently a divalent organic group optionally having an oxygen atom and/or a nitrogen atom.

However, most of the bifunctional (meth)acrylamide compounds represented by the general formula (5) have the following disadvantages. These compounds are solid in nature and have poor compatibility with other monomers. Therefore, in a dental composition containing this solid compound, deposition or phase separation of the monomers occurs, or phase separation of the components occurs when air-blowing is performed for use, resulting in low storage stability and poor adhesiveness to tooth structures. Some of the bifunctional (meth)acrylamide compounds represented by the general formula (5) are oily in nature and have good compatibility with other monomers, but a dental composition containing this oily compound has the disadvantage of low adhesiveness to tooth structures. Furthermore, the bifunctional (meth)acrylamide compounds represented by the general formula (6) are also oily in nature and have good compatibility with other monomers, but a dental composition containing this oily compound has the disadvantage of low adhesiveness to tooth structures.

Patent Literature 2 proposes a dental adhesive composition having a pH of at least 3 and suited for total etching. The dental adhesive composition proposed in this publication contains: a bifunctional (meth)acrylamide compound represented by the general formula (5) above having two (meth)acrylamide groups both of which are secondary amide groups, a bifunctional (meth)acrylamide compound represented by the general formula (6) above having two (meth)acrylamide groups both of which are tertiary amide groups, or a monofunctional (meth)acrylamide compound represented by general formula (7); a water-soluble polymerizable carboxylic acid; and a water-soluble organic solvent.

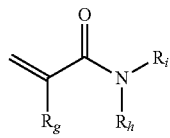

(7)

In general formula (7), $R_g$, $R_h$, and $R_i$ each independently represent a hydrogen atom, or a $C_1$ to $C_8$ alkyl group.

However, a disadvantage of this dental adhesive composition is that, because it is a dental adhesive composition suited for total etching, the dental adhesive composition has poor adhesiveness when used for bonding without phosphoric acid etching, that is, when used as a self-etching adhesive composition. The dental adhesive composition also has the same disadvantages as Patent Literature 1 when it contains a compound represented by general formula (5). Specifically, deposition or phase separation of the monomers occurs, or phase separation of the components occurs when air-blowing is performed for use, resulting in low storage stability and poor adhesiveness to tooth structures. The dental adhesive composition also suffers from poor adhesiveness to tooth structures when it contains a compound represented by general formula (6).

Patent Literature 3 proposes a dental composition containing: an acidic monomer; an asymmetric bifunctional (meth)acrylamide compound represented by the general formula (8) having two (meth)acrylamide groups, one of which is a secondary amide group and the other of which is a tertiary amide group (hereinafter, in the present description, a (meth)acrylamide compound having two (meth)acrylamide groups, one of which is a secondary amide group and the other of which is a tertiary amide group may be referred to as an asymmetric (meth)acrylamide compound, for the sake of convenience).

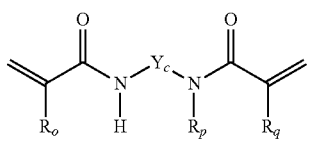

(8)

In general formula (8), $R_o$ and $R_q$ are each independently a hydrogen atom or a methyl group, $R_p$ represents a linear or branched $C_1$ to $C_4$ aliphatic group, and $Y_c$ is a divalent organic group optionally having an oxygen atom and/or a nitrogen atom.

The composition disclosed in Patent Literature 3 has good storage stability because its components are highly compatible with one another and thus difficult to separate from one another. This composition further has good initial bond strength to both dentin and enamel. This composition, however, has been found to have low bond durability, and poor adhesiveness to tooth structures subjected to phosphoric acid. Subsequent studies by the present inventors have revealed that this composition still has room for improvement.

Patent Literature 4 proposes an adhesive component containing a carboxamide group-containing (meth)acrylic acid ester and suitable for treatment of collagen-containing materials such as bones and teeth.

The composition disclosed in Patent Literature 4 is proposed as an alternative treatment agent to acid etching agents but the etching effect of this composition on tooth structures is not strong enough, and thus has the disadvantage of low adhesiveness to both enamel and dentin.

CITATION LIST

Patent Literature

Patent Literature 1: JP 2002-212019 A
Patent Literature 2: JP 2009-542740 T
Patent Literature 3: JP 2013-209341 A
Patent Literature 4: JP 03(1991)-204846 A

SUMMARY OF INVENTION

Technical Problem

It is an object of the present invention to provide a self-etching dental adhesive that exhibits excellent initial bond strength and bond durability to not only dentin untreated by phosphoric acid etching, but to dentin treated by phosphoric acid etching.

Solution to Problem

A solution to the foregoing problems is provided by a dental adhesive containing:
a (meth)acrylamide compound (a);
an asymmetric acrylamide-methacrylic acid ester compound (b); and
an acid group-containing (meth)acrylic polymerizable monomer (c),
wherein the (meth)acrylamide compound (a) is at least one compound selected from the group consisting of compounds represented by the following general formula (1), and compounds represented by the following general formula (2), and
wherein the asymmetric acrylamide-methacrylic acid ester compound (b) is a compound represented by the following general formula (3),

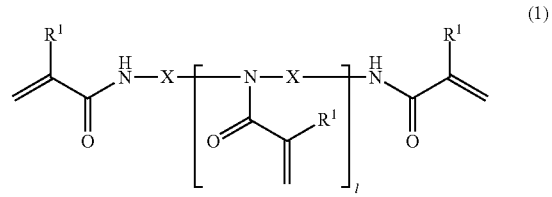

(1)

wherein R¹ represents a hydrogen atom or a methyl group, l represents an integer of 1 to 6, X represents an optionally substituted, linear or branched $C_1$ to $C_8$ alkylene group, the plurality of R¹ may be the same or different, and the plurality of X may be the same or different, (2)

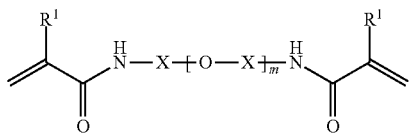

wherein m represents 2 or 3, R¹ and X are as defined above, the plurality of R¹ may be the same or different, and the plurality of X may be the same or different, (3)

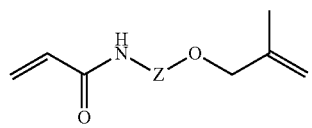

wherein Z is an optionally substituted, linear or branched $C_1$ to $C_8$ aliphatic group or an optionally substituted aromatic group, the aliphatic group being optionally interrupted by at least one linking group selected from the group consisting of —O—, —S—, —CO—, —CO—O—, —O—CO—, —NR²—, —CO—NR²—, —NR²—CO—, —CO—O—NR²—, —O—CONR²—, and —NR²—CO—NR²—, and R² represents a hydrogen atom, or an optionally substituted, linear or branched $C_1$ to $C_8$ aliphatic group.

Preferably, the dental adhesive further contains a hydrophilic polymerizable monomer (d).

It is preferable in the dental adhesive that the acid group-containing (meth)acrylic polymerizable monomer (c) is a phosphoric acid group-containing (meth)acrylic polymerizable monomer.

Preferably, the dental adhesive further contains a hydrophobic crosslinkable polymerizable monomer (e).

Preferably, the hydrophilic polymerizable monomer (d) contains a monofunctional (meth)acrylamide compound (d-1) represented by the following general formula (4), (4)

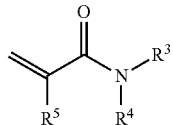

wherein R³ and R⁴ are each independently a $C_1$ to $C_3$ alkyl group, and R⁵ is a hydrogen atom or a methyl group.

It is preferable in the dental adhesive that the (meth)acrylamide compound (a) is at least one selected from the group consisting of the following compounds (a1-1), (a1-3), (a1-5), and (a1-7).

Compound (a1-1)

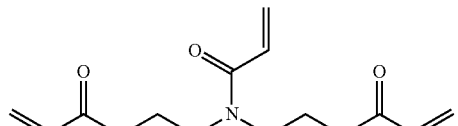

Compound (a1-3)

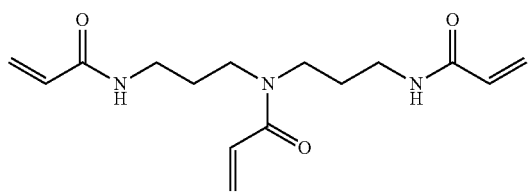

Compound (a1-5)

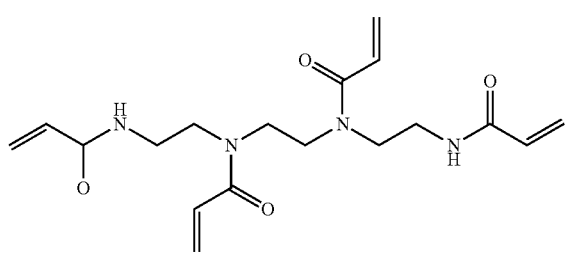

Compound (a1-7)

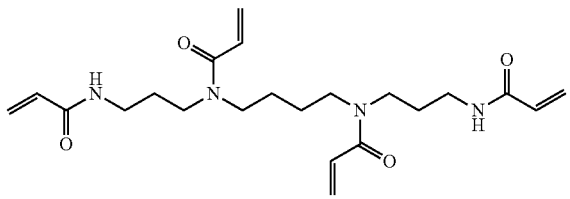

It is preferable in the dental adhesive that the (meth)acrylamide compound (a) is at least one selected from the group consisting of the following compounds (a2-1), (a2-3), (a2-5), (a2-7), and (a2-21).

Compound (a2-1)

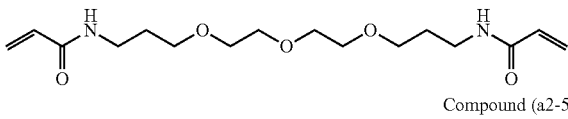

Compound (a2-3)

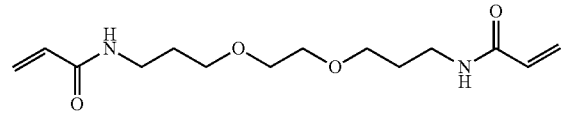

Compound (a2-5)

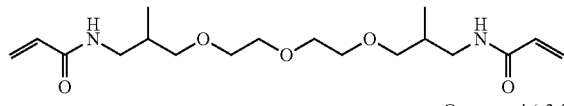

Compound (a2-7)

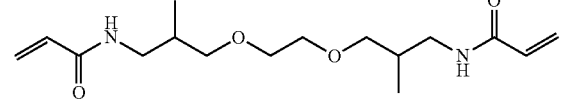

Compound a2-21)

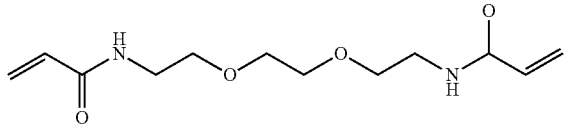

It is preferable in the dental adhesive that the (meth)acrylamide compound (a) is the following compound (a2-1).

Compound (a2-1)

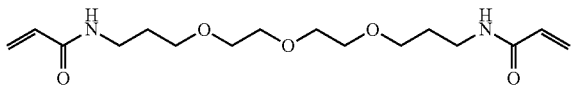

It is preferable in the dental adhesive that the (meth)acrylamide compound (a) is the following compound (a2-21).

Compound (a2-21)

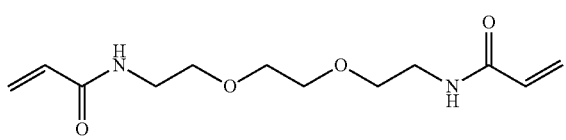

It is preferable in the dental adhesive that the asymmetric acrylamide-methacrylic acid ester compound (b) is a compound represented by the general formula (3) in which Z is an optionally substituted, linear or branched $C_2$ to $C_4$ aliphatic group.

It is preferable in the dental adhesive that the asymmetric acrylamide-methacrylic acid ester compound (b) is at least one selected from the group consisting of N-methacryloyloxyethylacrylamide, N-methacryloyloxypropylacrylamide, N-methacryloyloxybutylacrylamide, N-(1-ethyl-(2-methacryloyloxy) ethyl)acrylamide, and N-(2-(2-methacryloyloxyethoxy)ethyl)acrylamide).

Advantageous Effects of Invention

The present invention can provide a self-etching dental adhesive that exhibits excellent initial bond strength and bond durability not only to dentin untreated by phosphoric acid etching, but to dentin treated by phosphoric acid etching.

DESCRIPTION OF EMBODIMENTS

A dental adhesive of the present invention contains a (meth)acrylamide compound (a), an asymmetric acrylamide-methacrylic acid ester compound (b), and an acid group-containing (meth)acrylic polymerizable monomer (c) as essential components. As used in the present description, "(meth)acrylate" collectively refers to acrylate and methacrylate. The same applies to similar expressions.

A dental adhesive of the present invention is characterized in that it uses a (meth)acrylamide compound (a), and an asymmetric acrylamide-methacrylic acid ester compound (b). The (meth)acrylamide compound (a) is at least one selected from the group consisting of compounds represented by the general formula (1) above, and compounds represented by the general formula (2) above. The asymmetric acrylamide-methacrylic acid ester compound (b) is a compound represented by the general formula (3) above having two polymerizable groups, one of which is a methacrylic acid ester group and the other of which is an acrylamide group as a secondary amide group. (Hereinafter, in the present description, a compound having two polymerizable groups bonded to a group represented by Z, one of which is a methacrylic acid ester group and the other of which is an acrylamide group as a secondary amide group, is referred to as an "asymmetric acrylamide-methacrylic acid ester compound" for the sake of convenience.)

Phosphoric acid etching, which is usually highly demineralizing, is known to expose collagen fibers through demineralization of hydroxyapatite when applied to dentin, which contains organic material such as collagen. This makes the dentin structure brittle, and severely affects its adhesiveness. Further, the collagen in the exposed dentin contracts during rinsing and drying, and prevents smooth penetration of the bonding material. It has accordingly been difficult to provide high adhesiveness for dentin subjected to phosphoric acid etching.

It is not known exactly why a dental adhesive of the present invention containing a (meth)acrylamide compound (a) and an asymmetric acrylamide-methacrylic acid ester compound (b) exhibits high initial bond strength and bond durability also to dentin subjected to phosphoric acid etching. The reasons for this are probably as follows. The (meth)acrylamide compound (a) of the present invention has two amide protons, which make the compound very hydrophilic, and easily penetrate into the contracted collagen layer of dentin. The (meth)acrylamide compound (a) also has more than one polymerizable group within the molecule, and exhibits very high curability with the other components of the dental adhesive. The asymmetric acrylamide-methacrylic acid ester compound (b) has one amide proton, and shows high hydrophilicity, though not as high as that of the (meth)acrylamide compound (a). Further, the two polymerizable groups—the acrylamide group and the methacrylic acid ester group within the molecule—have relatively similar and balanced curing rates, and the asymmetric acrylamide-methacrylic acid ester compound (b) can exhibit sufficient curability, allowing the bonding material to form a strong layer upon penetrating into dentin. With the acrylamide group and the methacrylic acid ester group, the asymmetric acrylamide-methacrylic acid ester compound (b) is also believed to serve as a bridge between the (meth)acrylamide compound (a) having only a (meth)acrylamide group, and other dental adhesive monomers having only a (meth)acrylic acid ester group (for example, the acid group-containing (meth)acrylic polymerizable monomer (c)), and contribute to more efficient progression of the polymerization curing reaction in the dental adhesive composition system. With their high hydrophilicity, the two monomers—the (meth)acrylamide compound (a) and the asymmetric acrylamide-methacrylic acid ester compound (b)—seem to penetrate into the contracted collagen of dentin after a phosphoric acid etching treatment, and, by being highly curable, the bonding material probably forms a strong layer on the embrittled dentin.

These are the reasons that the dental adhesive using the (meth)acrylamide compound (a) and the asymmetric acrylamide-methacrylic acid ester compound (b) shows high initial bond strength and bond durability when used not only for self-etching but for dentin treated by phosphoric acid etching.

The following describes the (meth)acrylamide compound (a) used in the present invention. The (meth)acrylamide compound (a) is at least one selected from the group consisting of compounds represented by the following general formula (1), and compounds represented by the following general formula (2). The (meth)acrylamide compound (a) represented by formula (1) will be described first, followed by the (meth)acrylamide compound (a) represented by formula (2).

The following describes the (meth)acrylamide compound (a) represented by general formula (1).

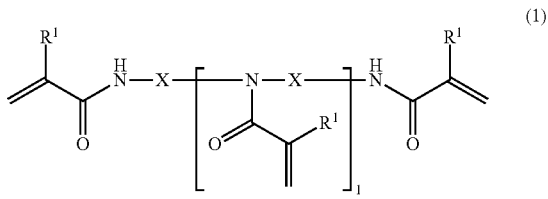

In general formula (1), $R^1$ represents a hydrogen atom or a methyl group, 1 represents an integer of 1 to 6, X represents an optionally substituted, linear or branched $C_1$ to $C_8$ alkylene group, the plurality of $R^1$ may be the same or different, and the plurality of X may be the same or different, Preferably, $R^1$ in formula (1) is a hydrogen atom in view of adhesiveness to tooth structures, and polymerization curability.

Preferably, 1 is an integer of 1 to 4, more preferably an integer of 1 to 3, particularly preferably an integer of 1 or 2.

X is a moiety for adjusting the hydrophilicity of the (meth)acrylamide compound (a). In view of adhesiveness to tooth structures, and polymerization curability, X in formula (1) is preferably an optionally substituted, linear or branched $C_1$ to $C_5$ alkylene group, further preferably an optionally substituted, linear or branched $C_2$ to $C_4$ alkylene group, particularly preferably an unsubstituted linear $C_2$ to $C_4$ alkylene group.

Examples of the linear or branched $C_1$ to $C_8$ alkylene group include methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, tetramethylene, 1-propylethylene, 2-propylethylene, 1-ethyl-1-methylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, 1-butylethylene, 2-butylethylene, 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 3-propyltrimethylene, 1-ethyl-1-methyltrimethylene, 1-ethyl-2-methyltrimethylene, 1-ethyl-3-methyltrimethylene, 2-ethyl-1-methyltrimethylene, 2-ethyl-2-methyltrimethylene, 2-ethyl-3-methyltrimethylene, 3-ethyl-1-methyltrimethylene, 3-ethyl-2-methyltrimethylene, 3-ethyl-3-methyltrimethylene, 1,1,2-trimethyltrimethylene, 1,1,3-trimethyltrimethylene, 1,2,2-trimethyltrimethylene, 1,2,3-trimethyltrimethylene, 1,3,3-trimethyltrimethylene, 2,2,3-trimethyltrimethylene, 2,3,3-trimethyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, 1-methylpentamethylene, 2-methylpentamethylene, 3-methylpentamethylene, 4-methylpentamethylene, 5-methylpentamethylene, hexamethylene, 2,2,3-trimethyltetramethylene, 3-ethylpentamethylene, 2,2-dimethylpentamethylene, 2,3-dimethylpentamethylene, 2,4dimethylpentamethylene, 3,3-dimethylpentamethylene, 2-methylhexamethylene, 3-methylhexamethylene, heptamethylene, 2,2,3,3-tetramethyltetramethylene, 2,2,3-trimethylpentamethylene, 2,2,4-trimethylpentamethylene, 2,3,3-trimethylpentamethylene, 2,3,4-trimethylpentamethylene, 3-ethyl-2-methylpentamethylene, 3-ethyl-3-methylpentamethylene, 2,2-dimethylhexamethylene, 2,3-dimethylhexamethylene, 2,4-dimethylhexamethylene, 2,5-dimethylhexamethylene, 3,3-dimethylhexamethylene, 3,4-dimethylhexamethylene, 3-ethylhexamethylene, 2-methylheptamethylene, 3-methylheptamethylene, 4-methylheptamethylene, and octamethylene groups. Preferred are methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, and tetramethylene groups. More preferred are methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, and tetramethylene groups.

The substituents of X are not particularly limited. Examples include halogen atoms (a fluorine atom, a chlorine atom, a bromine atom, an iodine atom), a carboxy group, a hydroxyl group, an amino group, an amino group monosubstituted or disubstituted with a $C_1$ to $C_8$ alkyl group, an acyl group, an acyloxy group, an amide group, a $C_2$ to $C_8$ alkoxycarbonyl group, a $C_1$ to $C_8$ alkoxy group, a $C_1$ to $C_8$ alkylthio group, and a $C_1$ to $C_8$ alkyl group. More preferred are, for example, halogen atoms (a fluorine atom, a chlorine atom, a bromine atom, an iodine atom), and a $C_1$ to $C_8$ alkyl group. The $C_2$ to $C_8$ alkoxycarbonyl group, the $C_1$ to $C_8$ alkoxy group, the $C_1$ to $C_8$ alkylthio group, and the $C_1$ to $C_8$ alkyl group may be substituted with one, two, or three halogen atoms. Preferred as the alkyl group is a linear or branched $C_1$ to $C_4$ alkyl group. The number of substituents is not particularly limited, and may be about 1 to 8, preferably 1, 2, or 3.

The $C_1$ to $C_8$ alkyl group may be linear or branched. Examples include methyl, ethyl, n-propyl, isopropyl, n-butyl, isobutyl, sec-butyl, tert-butyl, n-pentyl, isopentyl, sec-pentyl, neopentyl, tert-pentyl, 1-ethylpropyl, n-hexyl, isohexyl, 1,1-dimethylbutyl, 2,2-dimethylbutyl, 3,3-dimethylbutyl, 2-ethylbutyl, n-heptyl, isoheptyl, 1,1-dimethylpentyl, 2,2-dimethylpentyl, 3,3-dimethylpentyl, 4,4-dimethylpentyl, 2-ethylpentyl, n-octyl, isooctyl, 1,1-dimethylhexyl, 2,2-dimethylhexyl, 3,3-dimethylhexyl, 4,4-dimethylhexyl, 5,5-dimethylhexyl, and 2-ethylhexyl groups. Preferred are, for example, methyl, ethyl, n-propyl, isopropyl, n-butyl, isobutyl, sec-butyl, and tert-butyl groups.

The following are specific examples of the tri- or higher-functional (meth)acrylamide compounds (a) represented by formula (1). The present invention, however, is not limited to these.

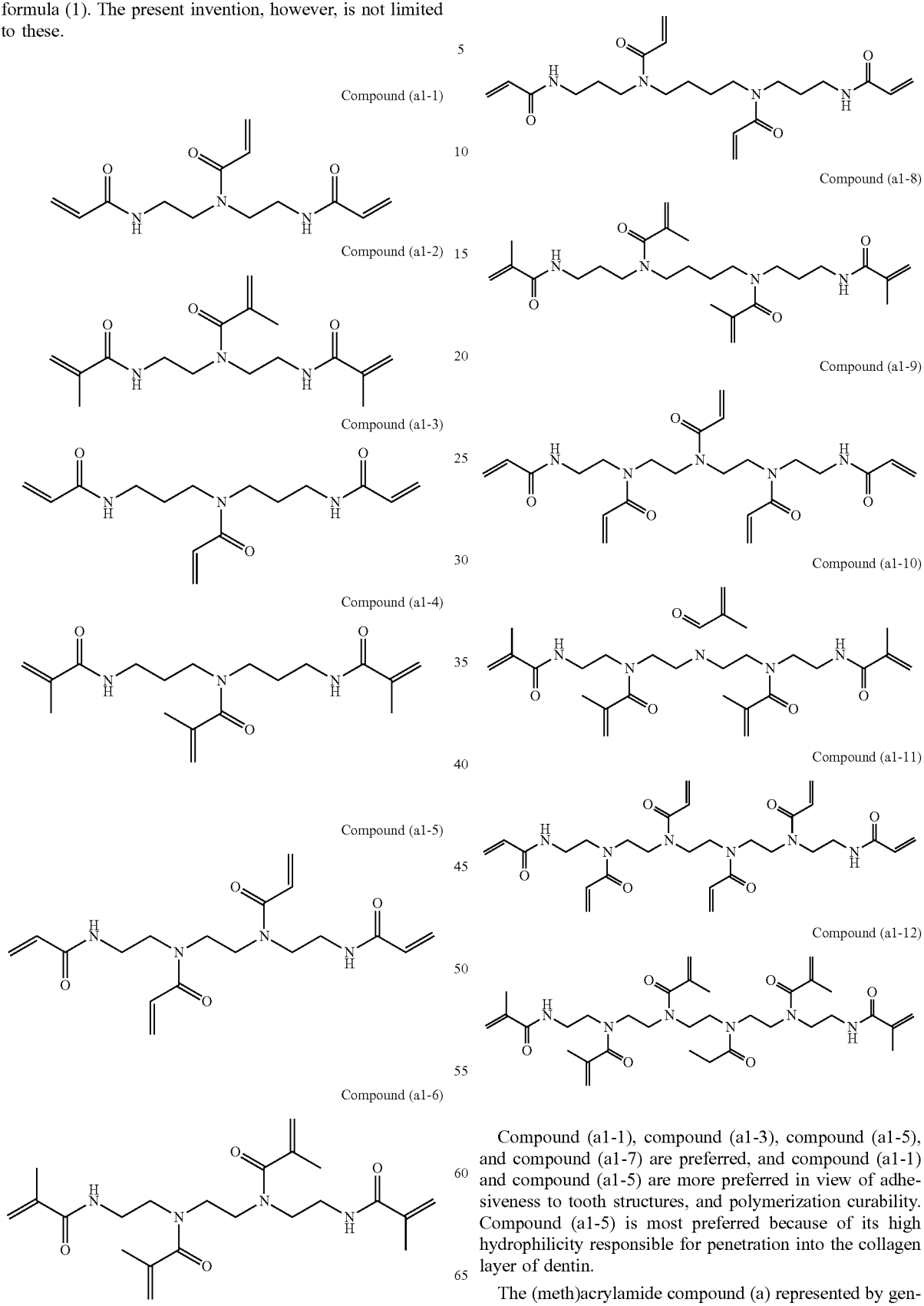

Compound (a1-1), compound (a1-3), compound (a1-5), and compound (a1-7) are preferred, and compound (a1-1) and compound (a1-5) are more preferred in view of adhesiveness to tooth structures, and polymerization curability. Compound (a1-5) is most preferred because of its high hydrophilicity responsible for penetration into the collagen layer of dentin.

The (meth)acrylamide compound (a) represented by general formula (2) is described below.

(2)

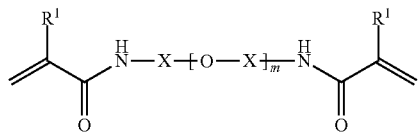

In general formula (2), m represents 2 or 3, $R^1$ and X are as defined above, the plurality of $R^1$ may be the same or different, and the plurality of X may be the same or different.

Preferably, m is 3. $R^1$ in formula (2) is preferably a hydrogen atom in view of adhesiveness to tooth structures, and polymerization curability. In view of adhesiveness to tooth structures, and polymerization curability, X in formula (2) is preferably an optionally substituted, linear or branched $C_1$ to $C_5$ alkylene group, further preferably an optionally substituted, linear or branched $C_2$ to $C_4$ alkylene group, particularly preferably an unsubstituted linear $C_2$ to $C_4$ alkylene group.

The following are specific examples of the bifunctional (meth)acrylamide compounds (a) represented by formula (2). The present invention, however, is not limited to these.

Compound (a2-1)

Compound (a2-2)
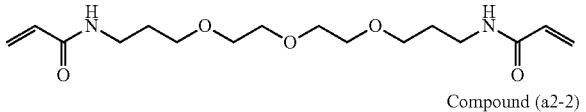

Compound (a2-3)
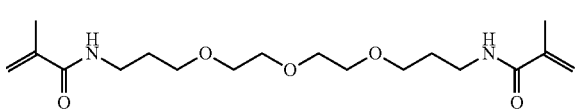

Compound (a2-4)
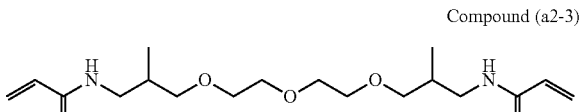

Compound (a2-5)
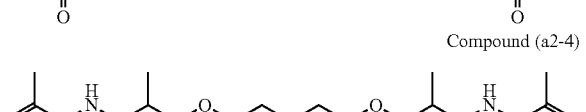

Compound (a2-6)
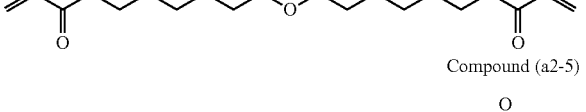

Compound (a2-7)
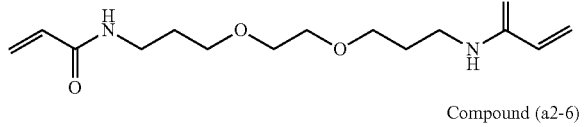

Compound (a2-8)
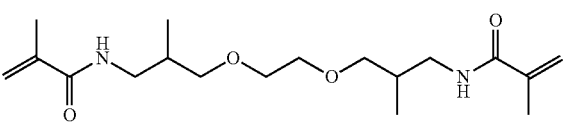

Compound (a2-9)
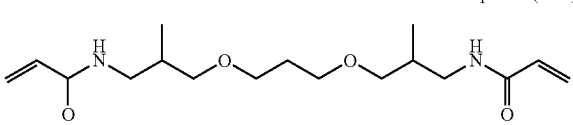

Compound (a2-10)
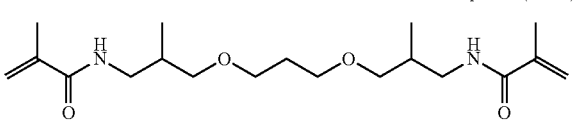

Compound (a2-11)
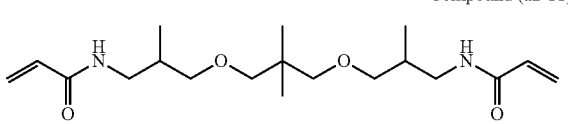

Compound (a2-12)
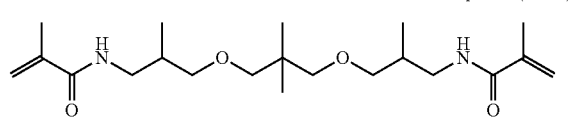

Compound (a2-13)
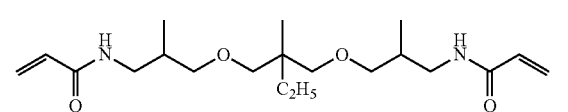

Compound a2-14)
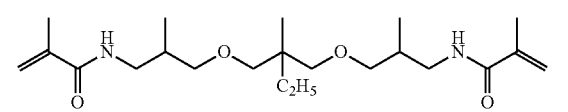

Compound (a2-15)
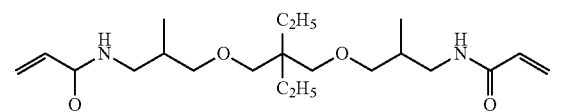

Compound (a2-16)
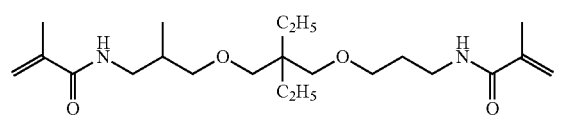

Compound (a2-17)
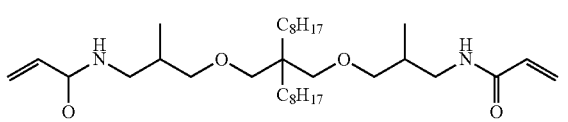

Compound (a2-18)
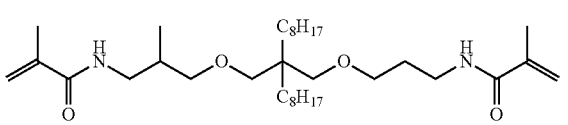

Compound (a2-19)

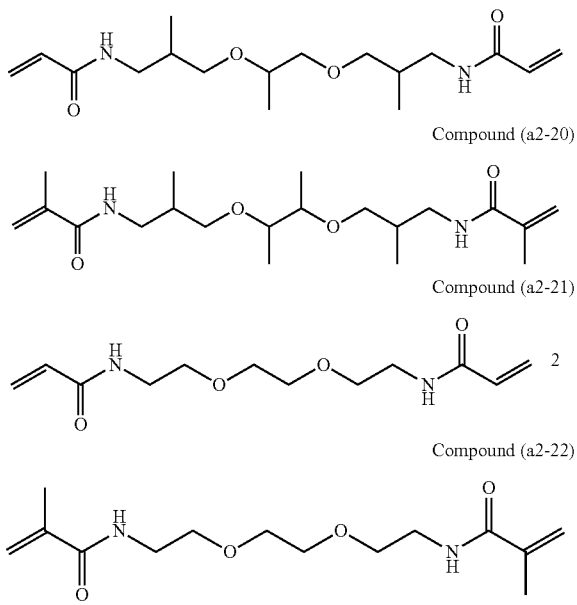

Compound (a2-1), compound (a2-3), compound (a2-5), compound (a2-7), and compound (a2-21) are preferred, and compound (a2-1), compound (a2-3), and compound (a2-21) are more preferred in view of adhesiveness to tooth structure, and polymerization curability. Compound (a2-1) and compound (a2-21) are further preferred, and compound (a2-1) is most preferred because of their high hydrophilicity responsible for penetration into the collagen layer of dentin.

The (meth)acrylamide compounds (a) may be contained either alone or in a combination of two or more. The content of the (meth)acrylamide compound (a) is not particularly limited, as long as the effect of the present invention can be obtained. However, the content of the (meth)acrylamide compound (a) is preferably in the range of 0.1 to 50 weight %, more preferably 0.3 to 40 weight %, further preferably 0.5 to 30 weight %, particularly preferably 1.0 to 20 weight % with respect to the total weight of the dental adhesive (hereinafter, the "total weight of the dental adhesive" refers to the total weight of the dental adhesive including a polymerization initiator, a solvent, a polymerization accelerator, a polymerization inhibitor, a filler, and others).

The asymmetric acrylamide-methacrylic acid ester compound (b) used in the present invention is described below. The asymmetric acrylamide-methacrylic acid ester compound (b) is represented by the following general formula (3) (hereinafter, an asymmetric acrylamide-methacrylic acid ester compound represented by the following general formula (3) is referred to as an "asymmetric acrylamide-methacrylic acid ester compound (b)").

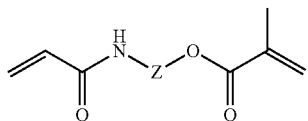

(3)

In general formula (3), Z is an optionally substituted, linear or branched $C_1$ to $C_8$ aliphatic group, or an optionally substituted aromatic group, and the aliphatic group may be interrupted by at least one linking group selected from the group consisting of —O—, —S—, —CO—, —CO—O—, —O—CO—, —NR$^2$—, —CO—NR$^2$—, —NR$^2$—CO—, —CO—O—NR$^2$—, —O—CONR$^2$—, and —NR$^2$—CO—NR$^2$—. That is, at least one of these linking groups may be introduced into the aliphatic group. $R^2$ represents a hydrogen atom, or an optionally substituted, linear or branched $C_1$ to $C_8$ aliphatic group.

Z is a moiety for adjusting the hydrophilicity of the asymmetric acrylamide-methacrylic acid ester compound (b). The optionally substituted $C_1$ to $C_8$ aliphatic group represented by Z may be a saturated aliphatic group (such as an alkylene group or a cycloalkylene group (for example, 1,4-cyclohexylene group)) or an unsaturated aliphatic group (such as an alkenylene group or an alkynylene group). In view of availability, ease of production, and chemical stability, it is preferable that the aliphatic group be a saturated aliphatic group (alkylene group). In view of adhesiveness to tooth structures and polymerization curability, Z is preferably an optionally substituted, linear or branched $C_1$ to $C_4$ aliphatic group, and more preferably an optionally substituted, linear or branched $C_2$ to $C_4$ aliphatic group. Examples of the $C_1$ to $C_8$ alkylene group include those exemplified for X.

Examples of the optionally substituted aromatic group represented by Z include an aryl group and an aromatic heterocyclic group. An aryl group is more preferred than an aromatic heterocyclic group as the aromatic group mentioned above. The hetero ring of the aromatic heterocyclic group is usually unsaturated. The aromatic hetero ring is preferably a five-membered or six-membered ring. For example, a phenyl group is preferred as the aryl group. Examples of the aromatic heterocyclic group include furan, thiophene, pyrrole, oxazole, isoxazole, thiazole, isothiazole, imidazole, pyrazole, furazan, triazole, pyran, pyridine, pyridazine, pyrimidine, pyrazine, and 1,3,5-triazine groups. Among the aromatic groups mentioned above, a phenyl group is particularly preferred.

The aliphatic group as $R^2$ may be either a saturated aliphatic group (alkyl group) or an unsaturated aliphatic group (alkenyl or alkynyl group). In view of availability, ease of production, and chemical stability, the aliphatic group is preferably a saturated aliphatic group (alkyl group). Examples of the alkyl group include those described above as the substituents of X.

$R^2$ is more preferably a hydrogen atom, or an optionally substituted, linear or branched $C_1$ to $C_4$ alkyl group, and even more preferably a hydrogen atom, or an optionally substituted, linear or branched $C_1$ to $C_3$ alkyl group.

When the aliphatic group as Z is interrupted by the above-mentioned linking group(s), the number of the linking groups is not particularly limited. The number of the linking groups may be about 1 to 10, preferably 1, 2, or 3, and more preferably 1 or 2. In the above formula (3), it is preferable that the aliphatic group as Z be not interrupted by two or more contiguous linking groups. That is, it is preferable that the linking groups be not adjacent to each other. The linking group is more preferably at least one linking group selected from the group consisting of —O—, —S—, —CO—, —CO—O—, —O—CO—, —NH—, —CO—NH—, —NH—CO—, —CO—O—NH—, —O—CO—NH—, and —NH—CO—NH—, and particularly preferably at least one linking group selected from the group consisting of —O—, —S—, —CO—, —NH—, —CO—NH—, and —NH—CO—.

Examples of the substituents of Z include those exemplified above for the substituents of X.

Specific examples of the asymmetric acrylamide-methacrylic acid ester compound (b) are not particularly limited, and include the following.

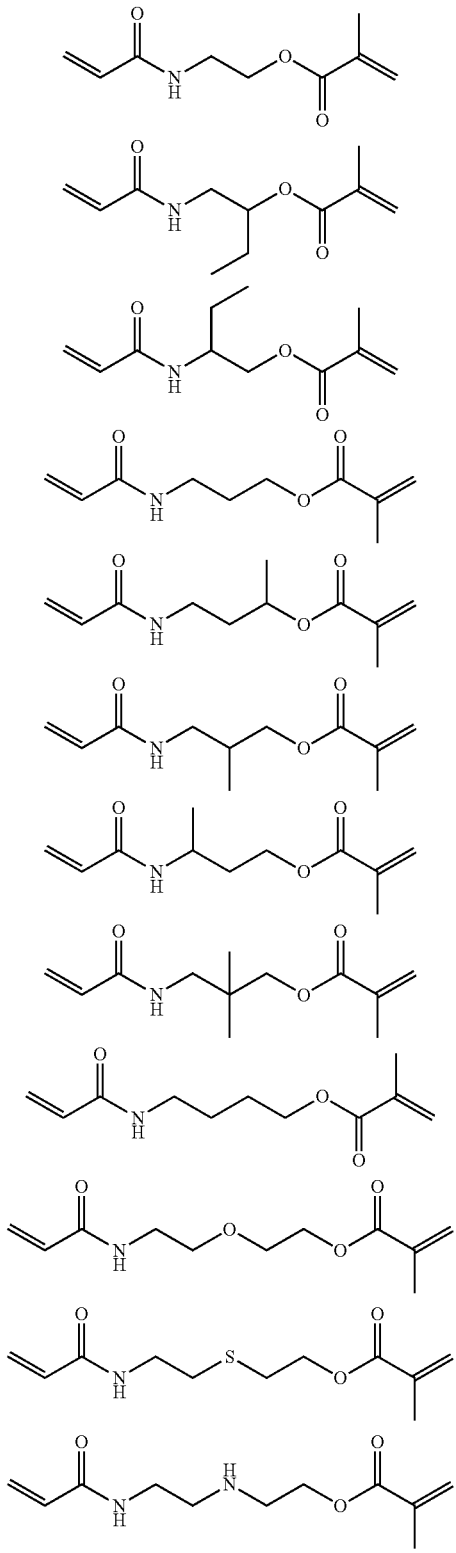

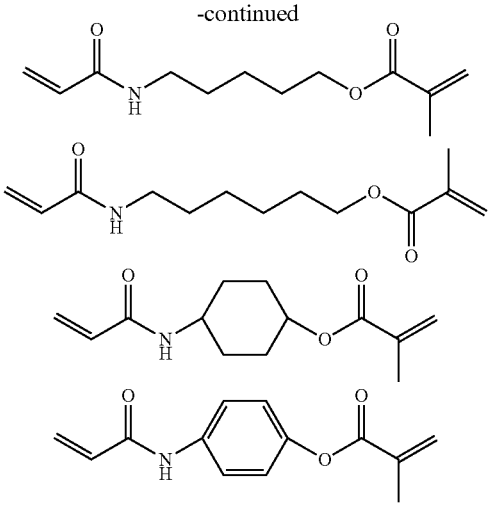

Among these, an asymmetric acrylamide-methacrylic acid ester compound (b) having an optionally substituted, linear or branched $C_2$ to $C_4$ aliphatic group as Z is preferred in view of adhesiveness to tooth structures and polymerization curability. N-Methacryloyloxyethyl acrylamide, N-methacryloyloxypropyl acrylamide, N-methacryloyloxybutyl acrylamide, N-(1-ethyl-(2-methacryloyloxy)ethyl) acrylamide, or N-(2-(2-methacryloyloxyethoxy)ethyl) acrylamide is more preferred. N-Methacryloyloxyethyl acrylamide or N-methacryloyloxypropyl acrylamide is most preferred because of its high hydrophilicity responsible for penetration into the collagen layer of dentin.

The asymmetric acrylamide-methacrylic acid ester compounds (b) may be contained either alone or in a combination of two or more. The content of the asymmetric acrylamide-methacrylic acid ester compound (b) is not particularly limited, as long as the effect of the present invention can be obtained. The content of the asymmetric acrylamide-methacrylic acid ester compound (b) is preferably in the range of 1 to 60 weight %, more preferably in the range of 2 to 45 weight %, even more preferably in the range of 3 to 30 weight %, and particularly preferably in the range of 5 to 25 weight % with respect to the total weight of the dental adhesive.

In the present invention, the weight ratio ((b):(a)) of the asymmetric acrylamide-methacrylic acid ester compound (b) to the (meth)acrylamide compound (a) is preferably 15:1 to 1:15, more preferably 12:1 to 1:12, particularly preferably 9:1 to 1:9. Containing the asymmetric acrylamide-methacrylic acid ester compound (b) in greater amounts (amounts exceeding the weight ratio ((b):(a)) of 15:1) may result in reduced adhesiveness to dentin subjected to phosphoric acid etching. The bond strength to enamel may weaken when the (meth)acrylamide compound (a) is contained in greater amounts (amounts exceeding the weight ratio ((b):(a)) of 1:15).

Next, the acid group-containing (meth)acrylic polymerizable monomer (c) used in the present invention is described. In the present invention, the (meth)acrylic polymerizable monomer refers to a (meth)acrylate compound and/or a (meth)acrylamide compound. The acid group-containing (meth)acrylic polymerizable monomer (c) demineralizes and penetrates into a tooth structure, and binds to the tooth structure. The acid-group-containing (meth)acrylic polymerizable monomer (c) is a polymerizable monomer having at least one acid group, for example, such as a phosphoric acid group, a phosphonic acid group, a pyrophosphoric acid group, a carboxylic acid group, and a sulfonic acid group, and at least one polymerizable group, for example, such as an acryloyl group, a methacryloyl group, an acrylamide group, and a methacrylamide group. In view of adhesiveness to enamel, the acid group-containing (meth)acrylic polymerizable monomer (c) is preferably a monofunctional monomer having any one of an acryloyl group, a methacryloyl group, an acrylamide group, and a methacrylamide group as a polymerizable group. Specific examples thereof are as follows.

Examples of the phosphoric acid group-containing (meth) acrylic polymerizable monomer include phosphoric acid group-containing monofunctional (meth)acrylate compounds such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth) acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth) acryloyloxyethylphenyl hydrogen phosphate, 2-(meth)acryloyloxyethyl-2-bromoethyl hydrogen phosphate, 2-(meth) acryloyloxyethyl-(4-methoxyphenyl) hydrogen phosphate, and 2-(meth)acryloyloxypropyl-(4-methoxyphenyl) hydrogen phosphate, and acid chlorides, alkali metal salts, ammonium salts, and amine salts thereof. Other examples include phosphoric acid group-containing bifunctional (meth)acrylate compounds such as bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, and 1,3-di (meth)acryloyloxypropyl dihydrogen phosphate, and acid chlorides, alkali metal salts, ammonium salts, and amine salts thereof.

Examples of the phosphonic acid group-containing (meth)acrylic polymerizable monomer include 2-(meth) acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and 10-(meth) acryloyloxydecylphosphonoacetate, and acid chlorides, alkali metal salts, ammonium salts, and amine salts thereof.

Examples of the pyrophosphoric acid group-containing (meth)acrylic polymerizable monomer include bis[2-(meth) acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, and bis[10-(meth)acryloyloxydecyl]pyrophosphate, and acid chlorides, alkali metal salts, ammonium salts, and amine salts thereof.

Examples of the carboxylic acid group-containing (meth) acrylic polymerizable monomer include (meth)acrylic acid, 4-(meth)acryloyloxyethoxycarbonylphthalic acid, 4-(meth) acryloxyethyl trimellitic acid, 4-(meth)acryloyloxybutyloxycarbonylphthalic acid, 4-(meth)acryloyloxyhexyloxycarbonylphthalic acid, 4-(meth) acryloyloxyoctyloxycarbonylphthalic acid, and 4-(meth) acryloyloxydecyloxycarbonylphthalic acid, and acid anhydrides thereof and 5-(meth)acryloylaminopentylcarboxylic acid, 6-(meth)acryloyloxy-1, 1-hexanedicarboxylic acid, 8-(meth)acryloyloxy-1,1-octanedicarboxylic acid, 10-(meth)acryloyloxy-1,1-decanedicarboxylic acid, and 11-(meth)acryloyloxy-1,1-undecanedicarboxylic acid, and acid chlorides, alkali metal salts, ammonium salts, and amine salts thereof.

Examples of the sulfonic acid group-containing (meth) acrylic polymerizable monomer include 2-(meth)acrylamide-2-methylpropanesulfonic acid, and 2-sulfoethyl (meth) acrylate, and acid chlorides, alkali metal salts, ammonium salts and amine salts thereof.

Among these acid group-containing (meth)acrylic polymerizable monomers (c), the phosphoric or pyrophosphoric acid group-containing (meth)acrylic polymerizable monomers are preferred since such monomers provide better bond strength to tooth structures. More preferred are the phosphoric acid group-containing (meth)acrylic polymerizable monomers. Further preferred are the phosphoric acid group-containing (meth)acrylic monofunctional polymerizable monomers. Among these monomers, a phosphoric acid group-containing (meth)acrylic monofunctional polymerizable monomer having a $C_6$ to $C_{20}$ alkyl or alkylene group as the main chain within the molecule is particularly preferred, and a phosphoric acid group-containing (meth)acrylic monofunctional polymerizable monomer having a $C_8$ to $C_{12}$ alkylene group as the main chain within the molecule (for example, 10-methacryloyloxydecyl dihydrogen phosphate) is most preferred.

The acid group-containing (meth)acrylic polymerizable monomers (c) may be contained either alone or in a combination of two or more. The content of the acid group-containing (meth)acrylic polymerizable monomer (c) is not particularly limited, as long as the effect of the present invention can be obtained. However, in order to obtain higher bond strength, the content of the acid group-containing (meth)acrylic polymerizable monomer (c) is preferably in the range of 1 to 50 weight %, more preferably in the range of 1 to 30 weight %, and most preferably in the range of 3 to 20 weight %, with respect to the total weight of the dental adhesive.

Next, the hydrophilic polymerizable monomer (d) is described.

In the context of the present invention, the hydrophilic polymerizable monomer (d) refers to a polymerizable monomer having a solubility of 5 weight % or more in water at 25° C., excluding the compounds (a), (b), (c), and (e). The hydrophilic polymerizable monomer (d) preferably has a solubility of 10 weight % or more, and more preferably a solubility of 15 weight % or more in water at 25° C. The hydrophilic polymerizable monomer (d) promotes penetration of the acid group-containing (meth)acrylic polymerizable monomer (c), the hydrophobic crosslinkable polymerizable monomer (e), and the polymerization initiator into a tooth structure. The monomer (d) itself also penetrates into a tooth structure and binds and adheres to an organic component (collagen) in the tooth structure.

Since the hydrophilic polymerizable monomer (d) has water solubility, it has a hydrophilic group such as a hydroxyl group, an oxymethylene group, an oxyethylene group, an oxypropylene group, or an amide group. Examples of the hydrophilic polymerizable monomer (d) include: water-soluble (meth)acrylate compounds such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-trimethylammoniumethyl (meth)acrylchloride, and polyethylene glycol di(meth)acrylate (having 9 or more oxyethylene groups); N-methylol (meth)acrylamide; N-hydroxyethyl (meth)acrylamide; N,N-(dihydroxyethyl) (meth)acrylamide; N-methoxymethyl (meth)acrylamide; N-ethoxymethyl (meth)acrylamide; diacetone (meth)acrylamide; 4-(meth) acryloylmorpholine; N-trihydroxymethyl-N-methyl (meth) acrylamide; and a monofunctional (meth)acrylamide compound (d-1) represented by the following general formula (4).

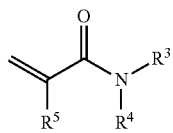

(4)

In the formula (4), $R^3$ and $R^4$ are each independently an optionally substituted, linear or branched $C_1$ to $C_3$ alkyl group, and $R^5$ is a hydrogen atom or a methyl group.

The same substituents exemplified for X in the general formulae (1) and (2) can be used as the substituents of $R^3$ and $R^4$. Examples of the above-mentioned $C_1$ to $C_3$ alkyl group as $R^3$ or $R^4$ include a methyl group, an ethyl group, an n-propyl group, and an isopropyl group.

Among these hydrophilic polymerizable monomers (d), in view of adhesiveness to tooth structures, 2-hydroxyethyl (meth)acrylate, 2,3-dihydroxypropyl (meth)acrylate, diacetone (meth)acrylamide, and a monofunctional (meth)acrylamide compound (d-1) represented by general formula (4) are preferable, and a monofunctional (meth)acrylamide compound (d-1) represented by general formula (4) is more preferable. The hydrophilic polymerizable monomers (d) may be contained either alone or in a combination of two or more.

Among the monofunctional (meth)acrylamide compounds (d-1), in view of storage stability, N,N-dimethylacrylamide and N,N-diethylacrylamide are more preferable, and N,N-diethylacrylamide is most preferable.

In the present invention, the content of the hydrophilic polymerizable monomer (d) is not particularly limited, as long as the effect of the present invention can be obtained. However, in order to obtain higher adhesiveness, the content of the hydrophilic polymerizable monomer (d) is preferably in the range of 5 to 60 weight %, more preferably in the range of 7 to 50 weight %, even more preferably in the range of 10 to 45 weight %, and most preferably in the range of 13 to 40 weight %, with respect to the total weight of the dental adhesive.

The hydrophobic crosslinkable polymerizable monomer (e) is described below. The hydrophobic crosslinkable polymerizable monomer (e) is a hydrophobic compound having no acid group and having at least two polymerizable groups per molecule. As used herein, the term "hydrophobicity" refers to a solubility of less than 5 weight % in water at 25° C. Examples of the hydrophobic crosslinkable polymerizable monomer (e) include aromatic compound-based bifunctional polymerizable monomers, aliphatic compound-based bifunctional polymerizable monomers, and tri- or higher-functional polymerizable monomers.

Examples of the aromatic compound-based bifunctional polymerizable monomers include bifunctional(meth)acrylate compounds such as 2,2-bis((meth)acryloyloxyphenyl) propane, 2,2-bis[4-(3-(meth)acryloyloxy-2-hydroxypropoxy)phenyl]propane, 2,2-bis(4-(meth) acryloyloxyethoxyphenyl)propane, 2,2-bis(4-(meth) acryloyloxypolyethoxyphenyl)propane, 2,2-bis(4-(meth) acryloyloxydiethoxyphenyl)propane, 2,2-bis(4-(meth) acryloyloxytriethoxyphenyl)propane, 2,2-bis(4-(meth) acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2-(4-(meth) acryloyloxydiethoxyphenyl)-2-(4-(meth) acryloyloxyethoxyphenyl)propane, 2-(4-(meth) acryloyloxydiethoxyphenyl)-2-(4-(meth) acryloyloxytriethoxyphenyl)propan e, 2-(4-(meth) acryloyloxydipropoxyphenyl)-2-(4-(meth) acryloyloxytriethoxyphenyl)propane, 2,2-bis(4-(meth) acryloyloxypropoxyphenyl)propane, and 2,2-bis(4-(meth) acryloyloxyisopropoxyphenyl)propane. Among these, 2,2-bis[4-(3-(methacryloyloxy-2-hydroxypropoxy)phenyl] propane (commonly known as "Bis-GMA") is preferable.

Examples of the aliphatic compound-based bifunctional polymerizable monomers include bifunctional(meth)acrylate compounds such as glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth) acrylate, 1,10-decanediol di(meth)acrylate, and 2,2,4-trimethylhexamethylene bis(2-carbamoyloxyethyl) di(meth) acrylate. Among these, 2,2,4-trimethylhexamethylene bis(2-carbamoyloxyethyl) dimethacrylate (commonly known as "UDMA") is preferable.

Examples of the tri- or higher-functional polymerizable monomers include tri- or higher-functional (meth)acrylate compounds such as trimethylolpropane tri(meth)acrylate, trimethylolethane tri(meth)acrylate, trimethylolmethane tri (meth)acrylate, pentaerythritol tri(meth)acrylate, pentaerythritol tetra(meth)acrylate, dipentaerythritol penta(meth)acrylate, N,N'-(2,2,4-trimethylhexamethylene)-bis[2-(aminocarboxy)propane-1,3-diol]tetra(meth)acrylate, and 1,7-diacryloyloxy-2,2,6,6-tetra(meth)acryloyloxymethyl-4-oxaheptane. Among these, N,N'-(2,2,4-trimethylhexamethylene)-bis[2-(aminocarboxy)propane-1,3-diol]tetramethacrylate is preferable.

Among the above-mentioned hydrophobic crosslinkable polymerizable monomers (e), Bis-GMA and UDMA are more preferable, and Bis-GMA is even more preferable.

The hydrophobic crosslinkable polymerizable monomers (e) may be contained either alone or in a combination of two or more. The content of the hydrophobic crosslinkable polymerizable monomer (e) is not particularly limited, as long as the effect of the present invention can be obtained. However, in order to provide not only high penetrability into a tooth structure and thus excellent adhesiveness but also sufficient strength to the composition (adhesive), the content of the hydrophobic crosslinkable polymerizable monomer (e) is preferably in the range of 5 to 60 weight %, more preferably in the range of 10 to 50 weight %, even more preferably in the range of 12 to 40 weight %, and particularly preferably in the range of 15 to 30 weight %, with respect to the total weight of the dental adhesive.

The dental adhesive of the present invention may contain a polymerizable monomer other than the above-mentioned polymerizable monomers, as long as the effect of the present invention is not impaired. Concerning the polymerizable monomer, the dental adhesive of the present invention may contain a (meth)acrylamide compound, for example, such as a symmetric (meth)acrylamide compound, and an asymmetric bifunctional (meth)acrylamide compound, other than the (meth)acrylamide compound (a). However, it is preferable that the dental adhesive contain no such compound (be substantially free of such a compound). In the present description, the phrase "being substantially free of a component" means that the dental adhesive of the present invention contains no such component or contains only traces of the component to the extent that the effect of the dental adhesive of the present invention is not impaired. The symmetric (meth)acrylamide compound is, for example, a compound represented by the above formula (5) or (6) (in these formulae, what the symbols stand for is as described above). Specific examples of the symmetric (meth)acrylamide compound include bisacrylamide ethylene and N,N'-diethyl-1,3-propylene-bisacrylamide. The asymmetric bifunctional (meth)acrylamide compound is, for example, a compound represented by the above formula (8) (in this formula, what the symbols stand for is as described above). Specific examples of the asymmetric bifunctional (meth)acrylamide compound include N-ethyl-1,2-bis(acrylamide) ethane.

Depending on the specific embodiment employed, the dental adhesive of the present invention preferably contains a solvent (0f. Examples of the solvent (f) include water, an organic solvent, and a mixed solvent thereof.

A dental adhesive of the present invention containing water will promote the demineralizing action of the acid group-containing (meth)acrylic polymerizable monomer (c) on a tooth structure. The water used needs to be substantially free of impurities that adversely affect the adhesive properties. The water is preferably distilled water or ion-exchanged water. Having too low a water content could lead to a failure to provide a sufficient promoting effect on the demineralizing action, while having too high a water content could cause reduced adhesiveness. Thus, the water content is preferably in the range of 1 to 50 weight %, more preferably in the range of 5 to 30 weight %, and most preferably in the range of 10 to 20 weight %, with respect to the total weight of the dental adhesive.

A dental adhesive of the present invention containing an organic solvent will yield a further improvement in terms of adhesive properties, coating properties, and penetration into tooth structures, and the organic solvent contained will prevent the components of the composition (adhesive) from becoming separated from one another. The organic solvent used typically has a boiling point of 150° C. or lower under ordinary pressure, and has a solubility of 5 weight % or more in water at 25° C. The organic solvent more preferably has a solubility of 30 weight % or more in water at 25° C., and is most preferably soluble in water at 25° C. in any desired proportion.

Examples of the organic solvent include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Among these, a water-soluble organic solvent is preferable as the organic solvent in view of both safety for living organisms, and ease of removal by volatility. To be specific, ethanol, 2-propanol, 2-methyl-2-propanol, acetone, and tetrahydrofuran are preferable. Ethanol, 2-propanol, 2-methyl-2-propanol, and tetrahydrofuran are more preferable. The content of the organic solvent is not particularly limited. Some embodiments have no need to contain the organic solvent. In embodiments using the organic solvent, the content of the organic solvent is preferably in the range of 1 to 70 weight %, more preferably in the range of 5 to 50 weight %, and most preferably in the range of 10 to 30 weight %, with respect to the total weight of the dental adhesive.

In view of curability, the dental adhesive of the present invention preferably contains a polymerization initiator (g). The polymerization initiator (g) used in the present invention may be a commonly-known polymerization initiator. The polymerization initiator (g) may be a photopolymerization initiator (g-1) or a chemical polymerization initiator (g-2). The polymerization initiators (g) may be contained either alone or in a combination of two or more. The photopolymerization initiator (g-1) and the chemical polymerization initiator (g-2) may be used in combination.

Examples of the photopolymerization initiator (g-1) include (bis)acylphosphine oxides, water-soluble acylphosphine oxides, thioxanthones, quaternary ammonium salts of thioxanthones, ketals, α-diketones, coumarins, anthraquinones, benzoin alkyl ether compounds, and α-aminoketone compounds.

Among the (bis)acylphosphine oxides, examples of the acylphosphine oxide include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxide include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and bis (2,5,6-trimethylbenzoyl)-2,4,4-trimethylpentylphosphine oxide.

The water-soluble acylphosphine oxide preferably has an alkali metal ion, an alkaline earth metal ion, a pyridinium ion, or an ammonium ion in the acylphosphine oxide molecule. For example, the water-soluble acylphosphine oxide can be synthesized by a method disclosed in EP 0009348 B1 or JP 57-197289 A.

Specific examples of the water-soluble acylphosphine oxide include sodium monomethyl acetylphosphonate, sodium monomethyl (1-oxopropyl)phosphonate, sodium monomethyl benzoylphosphonate, sodium monomethyl (1-oxobutyl)phosphonate, sodium monomethyl (2-methyl-1-oxopropyl)phosphonate, sodium acetylphosphonate, sodium acetylmethylphosphonate, methyl 4-(hydroxymethoxyphosphinyl)-4-oxobutanoate sodium salt, methyl-4-oxo-4-phosphonobutanoate monosodium salt, acetylphenylphosphinate sodium salt, sodium (1-oxopropyl) pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-dimethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl) phosphonite sodium salt, (1,1-diethoxyethyl)methylphosphonite sodium salt, methyl(2-methyloxathiolan-2-yl)phosphinate sodium salt, methyl(2,4,5-trimethyl-1,3-dioxolan-2-yl)phosphinate sodium salt, methyl(1,1-dipropoxyethyl)

phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxyme sodium salt, 1-[(N-ethoxyimino)ethyl]methylphosphinate sodium salt, methyl(1-phenyliminoethyl)phosphinate sodium salt, methyl(1-phenylhydrazonoethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methylphosphinate sodium salt, formylmethylphosphinate sodium salt, (1,1-dimethoxypropyl)methylphosphinate sodium salt, methyl(1-oxopropyl)phosphinate sodium salt, (1,1-dimethoxypropyl)methylphosphinate dodecylguanidine salt, (1,1-dimethoxypropyl)methylphosphinate isopropylamine salt, acetylmethylphosphinate thiosemicarbazone sodium salt, 1,3,5-tributyl-4-methylamino-1,2,4-triazolium(1,1-dimethoxyethyl)-methylphosphinate, 1-butyl-4-butylaminomethylamino-3,5-dipropyl-1,2,4-triazolium(1,1-dimethoxyethyl)-methylphosphinate, 2,4,6-trimethylbenzoylphenylphosphine oxide sodium salt, 2,4,6-trimethylbenzoylphenylphosphine oxide potassium salt, and 2,4,6-trimethylbenzoylphenylphosphine oxide ammonium salt. Examples of the water-soluble acylphosphine oxide further include compounds as specified in JP 2000-159621 A.

Among these (bis)acylphosphine oxides and water-soluble acylphosphine oxides, particularly preferred are 2,4,6-trimethylbenzoyldiphenylphosphine oxide, 2,4,6-trimethylbenzoylmethoxyphenylphosphine oxide, bis-(2,4,6-trimethylbenzoyl)phenylphosphine oxide, and 2,4,6-trimethylbenzoylphenylphosphine oxide sodium salt.

Examples of the thioxanthones and the quaternary ammonium salts of thioxanthones include thioxanthone, 2-chlorothioxanthen-9-one, 2-hydroxy-3-(9-oxo-9H-thioxanthen-4-yloxy)-N,N,N-trimethyl-propanaminium chloride, 2-hydroxy-3-(1-methyl-9-oxo-9H-thioxanthen-4-yloxy)-N,N,N-trimethyl-1-propanaminium chloride, 2-hydroxy-3-(9-oxo-9H-thioxanthen-2-yloxy)-N,N,N-trimethyl-1-propanaminium chloride, 2-hydroxy-3-(3,4-dimethyl-9-oxo-9H-thioxanthen-2-yloxy)-N,N,N-trimethyl-1-propan aminium chloride, 2-hydroxy-3-(3,4-dimethyl-9H-thioxanthen-2-yloxy)-N,N,N-trimethyl-1-propanaminium chloride, and 2-hydroxy-3-(1,3,4-trimethyl-9-oxo-9H-thioxanthen-2-yloxy)-N,N,N-trimethyl-1-propanaminium chloride.

A particularly preferred thioxanthone among the above-mentioned thioxanthones is 2-chlorothioxanthen-9-one, and a particularly preferred quaternary ammonium salt of a thioxanthone among the above-mentioned quaternary ammonium salts of thioxanthones is 2-hydroxy-3-(3,4-dimethyl-9H-thioxanthen-2-yloxy)-N,N,N-trimethyl-1-propanaminium chloride.

Examples of the ketals include benzyl dimethyl ketal, and benzyl diethyl ketal.

Examples of the α-diketones include diacetyl, dibenzyl, camphorquinone, 2,3-pentadione, 2,3-octadione, 9,10-phenanthrenequinone, 4,4'-oxybenzyl, and acenaphthenequinone. Particularly preferred among these is camphorquinone, since it shows maximum absorption at a wavelength in the visible region.

Examples of the coumarin compounds include compounds disclosed in JP 9-3109 A and JP 10-245525 A, such as 3,3'-carbonylbis(7-diethylamino)coumarin, 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphto[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazoyl)-2,3,6,7-tetrahydro-1,1,7,7-tetramethyl-1H,5H,11H-[1]benzopyrano[6,7,8-ij]quinolizin-11-one.

Among the above-mentioned coumarin compounds, 3,3'-carbonylbis(7-diethylaminocoumarin) and 3,3'-carbonylbis(7-dibutylaminocoumarin) are preferable.

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ether compounds include benzoin methyl ether, benzoin ethyl ether, benzoin isopropyl ether, and benzoin isobutyl ether.

Examples of the α-aminoketone compounds include 2-methyl-1-[4-(methylthio)phenyl]-2-morpholinopropan-1-one.

It is preferable to use, among these photopolymerization initiators (g-1), at least one selected from the group consisting of (bis)acylphosphine oxides, salts thereof, α-diketones, and coumarin compounds. Use of such a photopolymerization initiator makes it possible to obtain a dental adhesive that has excellent photocurability in the visible and near-ultraviolet regions, and exhibits sufficiently high photocurability, regardless of whether the light source is a halogen lamp, a light-emitting diode (LED), or a xenon lamp.

An organic peroxide is preferably used as the chemical polymerization initiator (g-2) among the polymerization initiators used in the present invention. The organic peroxide used as the chemical polymerization initiator (g-2) is not particularly limited, and may be a commonly-known organic peroxide. Typical examples of the organic peroxide include ketone peroxides, hydroperoxides, diacyl peroxides, dialkyl peroxides, peroxyketals, peroxyesters, and peroxydicarbonates.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexine.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy) octane, and n-butyl 4,4-bis(t-butylperoxy)valerate.

Examples of the peroxyesters include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvaleric acid.

Examples of the peroxydicarbonates include di-3-methoxybutyl peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, the diacyl peroxides are preferably used in view of the overall balance of safety, storage stability, and radical formation potential. Among the diacyl peroxides, benzoyl peroxide is particularly preferably used.

The content of the polymerization initiator (g) used in the present invention is not particularly limited. In view of the curability, etc. of the resulting composition, the content of the polymerization initiator is preferably in the range of 0.01 to 10 weight %, more preferably in the range of 0.05 to 7 weight %, and most preferably in the range of 0.1 to 5 weight %, with respect to the total weight of the dental adhesive. When the content of the polymerization initiator (g) exceeds 10 weight %, if the polymerization initiator itself has low polymerization performance, sufficient adhesiveness may not be obtained and even deposition of the components of the dental adhesive composition may occur.

In a preferred embodiment, the polymerization initiator (g) is used in combination with a polymerization accelerator (h). Examples of the polymerization accelerator (h) that may be used in the present invention include amines, sulfinic acids, sulfinates, borate compounds, barbituric acid derivatives, triazine compounds, copper compounds, tin compounds, vanadium compounds, halogen compounds, aldehydes, thiol compounds, sulfites, hydrogen sulfites, and thiourea compounds.

The amines include aliphatic amines and aromatic amines. Examples of the aliphatic amine include: primary aliphatic amines such as n-butylamine, n-hexylamine, and n-octylamine; secondary aliphatic amines such as diisopropylamine, dibutylamine, and N-methylethanolamine; tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferably used in view of the curability and storage stability of the composition, and in particular, N-methyldiethanolamine and triethanolamine are more preferably used.

Examples of the aromatic amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino) benzoate, 4-(N,N-dimethylamino)benzophenone, butyl 4-dimethylaminobenzoate, and 4-(dimethylamino)benzonitrile. Among these, at least one selected from the group consisting of N,N-di(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone is preferably used in view of their ability to impart high curability to the composition.

Examples of the sulfinic acids and sulfinates include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred are sodium benzenesulfinate, sodium p-toluenesulfinate, and sodium 2,4,6-triisopropylbenzenesulfinate.

The borate compound is preferably an aryl borate compound. Specific examples of aryl borate compounds that are suitable for use include borate compounds having one aryl group per molecule, such as trialkylphenylboron, trialkyl(p-chlorophenyl)boron, trialkyl(p-fluorophenyl)boron, trialkyl [(3,5-bistrifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (their alkyl groups are each at least one selected from the group consisting of, for example, an n-butyl group, an n-octyl group, and an n-dodecyl group), and salts thereof (for example, sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compound include those that have two aryl groups per molecule, such as dialkyldiphenylboron, dialkyldi(p-chlorophenyl)boron, dialkyldi(p-fluorophenyl)boron, dialkyl[di(3,5-bis-trifluoromethyl)phenyl]boron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (their alkyl groups are each at least one selected from the group consisting of, for example, an n-butyl group, an n-octyl group, and an n-dodecyl group), and salts thereof (for example, sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compound further include those that have three aryl groups per molecule, such as monoalkyltriphenylboron, monoalkyltri(p-chlorophenyl)boron, monoalkyltri(p-fluorophenyl)boron, monoalkyltri[3,5-bis(trifluoromethyl)phenyl]boron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl)boron (their alkyl groups are each at least one selected from, for example, an n-butyl group, an n-octyl group, and an n-dodecyl group), and salts thereof (for example, sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compound further include those that have four aryl groups per molecule, such as tetraphenylboron, tetrakis(p-chlorophenyl)boron, tetrakis(p-fluorophenyl)boron, tetrakis[(3,5-bistrifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [(3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, and (p-octyloxyphenyl)triphenylboron, and salts thereof (for example, sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

In view of storage stability, it is more preferable to use the borate compounds having three or four aryl groups per molecule among the above-mentioned aryl borate compounds. The aryl borate compounds may be used either alone or in a combination of two or more.

Examples of the barbituric acid derivatives include: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids; and salts thereof (alkali metal salts and alkaline earth metal salts are particularly preferable). Examples of the salts of the barbituric acid derivatives include sodium 5-butylbarbiturate, sodium 1,3,5-trimethylbarbiturate, and sodium 1-cyclohexyl-5-ethylbarbiturate.

Examples of particularly preferred barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acid derivatives.

Examples of the triazine compounds include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Among the triazine compounds mentioned above as examples, 2,4,6-tris(trichloromethyl)-s-triazine is particularly preferable in terms of polymerization activity. In terms of storage stability, 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine are particularly preferable. The triazine compounds may be used either alone or as a mixture of two or more.

Examples of the copper compounds include copper acetylacetonate, copper(II) acetate, copper oleate, copper(II) chloride, and copper(II) bromide.

Examples of the tin compounds include di-n-butyltin dimaleate, di-n-octyltin dimaleate, di-n-octyltin dilaurate, and di-n-butyltin dilaurate. Preferred tin compounds are di-n-octyltin dilaurate, and di-n-butyltin dilaurate.

The vanadium compound is preferably a tetravalent and/or pentavalent vanadium compound. Examples of the tetravalent and/or pentavalent vanadium compound include compounds mentioned in JP 2003-96122 A, such as divanadium(IV) tetroxide, vanadium(IV) oxide acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) pentoxide, sodium metavanadate(V), and ammonium metavanadate(V).

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde. Among these, p-n-octyloxybenzaldehyde is preferably used in view of curability.

Examples of the thiol compounds include 3-mercaptopropyltrimethoxysilane, 2-mercaptobenzoxazole, decanethiol, and thiobenzoic acid.

Examples of the sulfites include sodium sulfite, potassium sulfite, calcium sulfite, and ammonium sulfite.

Examples of the hydrogen sulfites include sodium hydrogen sulfite, and potassium hydrogen sulfite.

Examples of the thiourea compounds include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

The polymerization accelerators (h) may be used either alone or in a combination of two or more. The content of the polymerization accelerator (h) used in the present invention is not particularly limited. In view of the curability, etc. of the resulting composition, the content of the polymerization accelerator is preferably in the range of 0.01 to 10 weight %, more preferably in the range of 0.05 to 7 weight %, and most preferably in the range of 0.1 to 5 weight %, with respect to the total weight of the dental adhesive. When the content of the polymerization accelerator (h) exceeds 10 weight %, if the polymerization initiator itself has low polymerization performance, sufficient adhesiveness may not be obtained.

Depending on the embodiment employed, the dental adhesive of the present invention preferably further contains a filler (i). The filler (i) is typically classified broadly into an organic filler, an inorganic filler, and an organic-inorganic composite filler.

Examples of the material of the organic filler include polymethyl methacrylate, polyethyl methacrylate, a methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone or as a mixture of two or more. The shape of the organic filler is not particularly limited, and the particle diameter of the filler used can be selected as appropriate. In view of characteristics such as the handling properties and the mechanical strength of the resulting composition, the average particle diameter of the organic filler is preferably 0.001 to 50 µm, more preferably 0.001 to 10 µm. In the present description, the average particle diameter of the filler means the average particle diameter of the primary particles of the filler (i.e., the average primary particle diameter).

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone or as a mixture of two or more. The shape of the inorganic filler is not particularly limited, and the particle diameter of the filler used can be selected as appropriate. In view of characteristics such as the handling properties and the mechanical strength of the resulting composition, the average particle diameter of the inorganic filler is preferably 0.001 to 50 µm, more preferably 0.001 to 10 µm.

Examples of the shape of the inorganic filler include an irregular shape and a spherical shape. It is preferable to use a spherical filler as the inorganic filler in order to enhance the mechanical strength of the composition. The term "spherical filler" as used herein refers to a filler whose particles are rounded in shape as observed in a unit area of a photograph of the filler taken with a scanning electron microscope (which will hereinafter be abbreviated as "SEM"), and have an average aspect ratio of 0.6 or more as calculated by dividing a diameter of each particle in a direction perpendicular to the maximum diameter of the particle by the maximum diameter. The average particle diameter of the spherical filler is preferably 0.1 µm or more in order to prevent a decrease in the fraction of the spherical filler filling the composition, and maintain the mechanical strength. The average particle diameter of the spherical filler is preferably 5 µm or less in order to make the surface area of the spherical filler sufficient for maintaining the mechanical strength of the resulting cured product.

The inorganic filler may be surface-treated beforehand with a commonly-known surface treatment agent such as a silane coupling agent where necessary in order to adjust the flowability of the composition. Examples of the surface treatment agent include vinyltrimethoxysilane, vinyltriethoxysilane, vinyltrichlorosilane, vinyltri(β-methoxyethoxy)silane, γ-methacryloyloxyp ropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is obtainable by adding a monomer compound to the above inorganic filler, forming the mixture into a paste, then subjecting the paste to polymerization, and grinding the resulting polymerization product. The organic-inorganic composite filler used may be, for example, a TMPT filler (obtainable by mixing trimethylolpropane methacrylate and a silica filler, subjecting the mixture to polymerization, and then grinding the resulting polymerization product). The shape of the organic-inorganic composite filler is not particularly limited, and the particle diameter of the filler used can be selected as appropriate. In view of characteristics such as the handling properties and the mechanical strength of the resulting composition, the average particle diameter of the organic-inorganic composite filler is preferably 0.001 to 50 µm, more preferably 0.001 to 10 µm.

In the present description, the average particle diameter of the filler (i) can be determined by the laser diffraction scattering method or by electron microscopic observation of the particles. Specifically, the laser diffraction scattering method is convenient for particle diameter measurement of particles with a diameter of 0.1 µm or more, and electron microscopic observation is convenient for particle diameter measurement of ultrafine particles with a diameter of less than 0.1 µm. The 0.1 µm diameter is a value measured by the laser diffraction scattering method.

To be more specific about the laser diffraction scattering method, for example, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

To be more specific about the electron microscopic observation, for example, the average particle diameter can be measured by taking a photograph of the particles with a scanning electron microscope (S-4000, manufactured by Hitachi, Ltd.) and measuring the particle diameters of (200 or more) particles observed in a unit area of a photograph taken with an image-analyzing particle size distribution analysis software (MacView manufactured by Mountech Co., Ltd.). In this case, the particle diameter of each particle is obtained as an arithmetic mean value of the longest and shortest dimensions thereof, and the average primary particle diameter is calculated from the number of the particles and their particle diameters.

In the present invention, two or more fillers of different materials, different particle size distributions, and different forms may be mixed or combined for use. Particles other than the filler (i) particles may be unintentionally contained as impurities, as long as the effect of the present invention is not impaired. The filler used in the present invention may be a commercially available product.

The content of the filler (i) used in the present invention is not particularly limited. The content of the filler (i) is preferably in the range of 0.1 to 30 weight %, more preferably in the range of 0.5 to 20 weight %, and most preferably in the range of 1.0 to 10 weight %, with respect to the total weight of the dental adhesive.

The dental adhesive of the present invention may also contain, for example, a pH adjuster, a polymerization inhibitor, a fluorine ion-releasing component, an ultraviolet absorber, a thickener, a colorant, a fluorescent agent, or a flavor, as long as the effect of the present invention is not impaired. Additionally, the dental adhesive may contain an antimicrobial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, and triclosan.

Preferably, the dental adhesive of the present invention is formulated to make the pH of the liquid (composition) 1.5 to 4.0, more preferably 1.8 to 3.5, most preferably 2.0 to 3.0. When the pH of the composition is less than 1.5, excessive demineralization occurs, and the adhesion decreases in total-etching, in which the composition is applied to a tooth surface after a phosphoric acid etching treatment. When the pH of the composition is more than 4.0, the demineralization effect weakens, and the adhesion decreases in self-etching.

The dental adhesive of the present invention shows excellent adhesiveness when used not only for self etching but for dentin treated by phosphoric acid etching.

The dental adhesive of the present invention can be used for applications such as a primer, and a bonding material. In this case, the composition may be used as a two-part product providing the components of the composition in two separate parts.

The (meth)acrylamide compound (a) and the asymmetric acrylamide-methacrylic acid ester compound (b) used in the present invention contain amide protons, which make the compounds highly hydrophilic, and easily penetrate into the collagen layer of dentin. Therefore, the dental adhesive of the present invention containing the (meth)acrylamide compound (a) and the asymmetric acrylamide-methacrylic acid ester compound (b) can be used particularly suitably as a dental primer. The dental adhesive of the present invention also contains the acid group-containing (meth)acrylic polymerizable monomer (c), and can be used as a dental self-etching primer.

Preferably, a primer using the dental adhesive of the present invention is a dental composition containing the (meth)acrylamide compound (a), the asymmetric acrylamide-methacrylic acid ester compound (b), the acid group-containing (meth)acrylic polymerizable monomer (c), the hydrophilic polymerizable monomer (d), and the solvent (f). Preferably, the composition further contains the polymerization initiator (g) and the polymerization accelerator (h). The polymerization accelerator (h) is preferably an amine.

It is preferable that the solvent (f) be used in the form of a mixed solvent of water and an organic solvent. The content of water in the mixed solvent is not particularly limited. The content of water is preferably 10 weight % or more, and more preferably 30 weight % or more. Depending on the embodiment employed, the primer need not contain any organic solvent.

The dental adhesive of the present invention also can preferably be used as a bonding material. A bonding material in a "two-step adhesive system" in which a primer and a bonding material are used in combination is preferably a dental composition containing the (meth)acrylamide compound (a), the asymmetric acrylamide-methacrylic acid ester compound (b), the acid group-containing (meth)acrylic polymerizable monomer (c), the hydrophilic polymerizable monomer (d), the hydrophobic crosslinkable polymerizable monomer (e), the polymerization initiator (g), and the filler (i). Preferably, the composition also contains the polymerization accelerator (h). The polymerization accelerator (h) is preferably an amine.

The dental adhesive of the present invention contains the (meth)acrylamide compound (a), the asymmetric acrylamide-methacrylic acid ester compound (b), and the acid group-containing (meth)acrylic polymerizable monomer (c), wherein the (meth)acrylamide compound (a) and the asymmetric acrylamide-methacrylic acid ester compound (b) have highly hydrophilic amide protons, which make the compounds easily penetrate into the collagen layer of dentin, and these compounds are highly curable because of the plurality of polymerizable groups contained in the compounds. The dental adhesive of the present invention can thus be advantageously applied to a "one-step adhesive system" in which the three steps of "demineralization", "penetration", and "curing" are performed in one operation. The bonding material used in such a one-step adhesive system is typically available in two different forms: a bonding material including two different liquids, liquid A and liquid B, to be mixed together immediately before use; and a bonding material that is available in one part, or a "one-part one-step adhesive system" as it is also called. Use of the one-part product is more advantageous because the process is simpler. Therefore, it is most preferable to use the dental adhesive of the present invention as a one-part bonding material. When the dental adhesive of the present invention is used as a one-part bonding material of a one-step adhesive system, it is preferable that the dental adhesive be a composition containing the (meth)acrylamide compound (a), the asymmetric acrylamide-methacrylic acid ester compound (b), the acid group-containing (meth)acrylic polymerizable monomer (c), the hydrophilic polymerizable monomer (d), the hydrophobic crosslinkable polymerizable monomer (e), the polymerization initiator (g), the filler (i), and the solvent (f), and it is more preferable that such a composition further contain a monofunctional (meth)acrylamide compound (d-1) as the hydrophilic polymerizable monomer (d). In the one-part one-step adhesive system, "penetration" and "curing" are performed in one operation. This is where the use of a polymerizable monomer having high hydrophilicity due to amide protons and having a plurality of polymerizable groups, specifically, the (meth) acrylamide compound (a) and the asymmetric acrylamide-methacrylic acid ester compound (b), is highly meaningful.

Preferably, the composition used for the one-part bonding material further contains the polymerization accelerator (h). The polymerization accelerator (h) is preferably an amine.

In the one-part one-step adhesive system, all the processes of demineralization, penetration, and curing need to be performed using one liquid in one step. Therefore, if priority is given to penetrability, it is preferable that the dental adhesive contain water as the solvent (f). On the other hand, if priority is given to curability, it is preferable that the dental adhesive contain an appropriate amount of the hydrophobic crosslinkable polymerizable monomer (e). In order to obtain a homogeneous solution, it is preferable that the dental adhesive contain an organic solvent as the solvent (f). Use of the solvent (f) in the form of a mixed solvent of water and an organic solvent is a more preferred embodiment. In such an embodiment, the content of water in the mixed solvent is preferably 5 weight % or more, more preferably 10 weight % or more, and even more preferably 20 weight % or more.

The dental adhesive according to the present invention exhibits excellent adhesiveness not only to tooth structures but also to crown restorative materials (such as metals, porcelains, ceramics, and cured composite resin materials) fractured in the oral cavity. In the case where the dental adhesive according to the present invention is used to bond a crown restorative material, the dental adhesive may be used in combination with a primer such as a commercially-available primer for metal bonding or porcelain bonding, or in combination with a tooth cleaning agent such as a hypochlorite or a hydrogen peroxide solution.

These dental adhesives can be prepared and used according to ordinary methods.

The present invention encompasses embodiments obtainable by combining the above configurations in various manners within the technical scope of the present invention, as long as the effect of the present invention can be obtained.

EXAMPLES

The present invention will be described in more detail by way of Examples. It should be noted that the present invention is in no way limited to the Examples given below, and the present invention can be implemented in various modifications within the technical ideas of the present invention by a person with common knowledge in the art (Meth)Acrylamide Compound (a)

TAC3: N,N',N''-Triacryloyldiethylenetriamine (compound (a1-1) represented by the following formula)

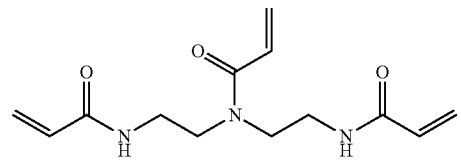 [SMILES: C=CC(=O)NCCN(CCNC(=O)C=C)C(=O)C=C]

TAC4: N,N',N'',N'''-Tetraacryloyltriethylenetetramine (compound (a1-5) represented by the following formula)

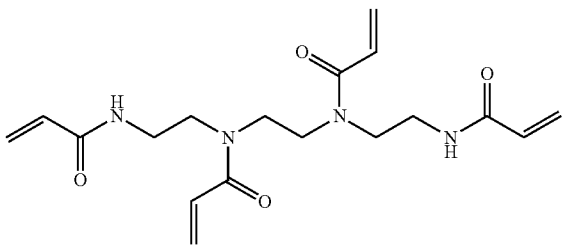 [SMILES: C=CC(=O)NCCN(CCN(CCNC(=O)C=C)C(=O)C=C)C(=O)C=C]

TOT-BA: N,N'-(4,7,10-Trioxatridecamethylene)-bisacrylamide (compound (a2-1) represented by the following formula)

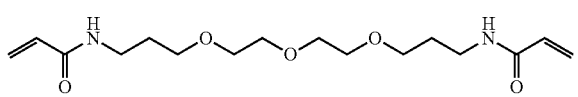 [SMILES: C=CC(=O)NCCCOCCOCCOCCCNC(=O)C=C]

TEGDAA: Triethylene glycol diacrylamide (compound (a2-21) represented by the following formula)

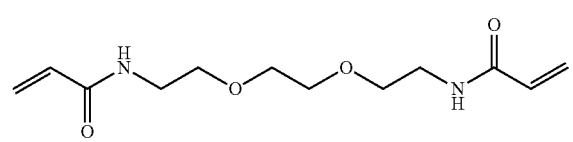 [SMILES: C=CC(=O)NCCOCCOCCNC(=O)C=C]

Asymmetric Acrylamide-Methacrylic Acid Ester Compound (b)

MAEA: N-Methacryloyloxyethylacrylamide (asymmetric acrylamide-methacrylic acid ester compound represented by the following formula)

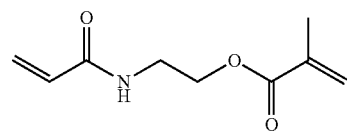

MAPA: N-Methacryloyloxypropylacrylamide (asymmetric acrylamide-methacrylic acid ester compound represented by the following formula)

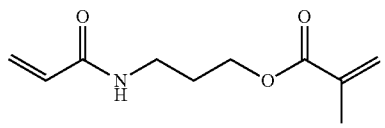

MAEEA: N-(1-Ethyl-(2-methacryloyloxy)ethyl)acrylamide (asymmetric acrylamide-methacrylic acid ester compound represented by the following formula)

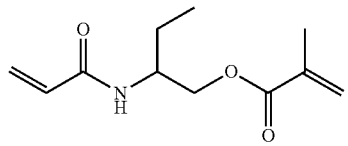

MAEGA: N-(2-(2-Methacryloyloxyethoxy)ethyl)acrylamide (asymmetric acrylamide-methacrylic acid ester compound represented by the following formula)

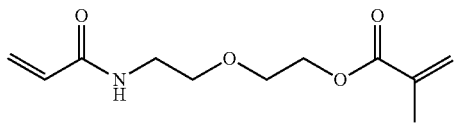 [SMILES: C=CC(=O)NCCOCCOC(=O)C(=C)C]

Symmetric Methacrylamide-Methacrylic Acid Ester Compound
MAEM: N-Methacryloyloxyethylmethacrylamide (symmetric methacrylamide-methacrylic acid ester compound represented by the following formula)

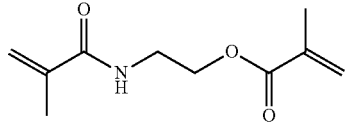

Asymmetric (Meth)Acrylamide Compound
NEBAE: N-Ethyl-1,2-bis(acrylamide)ethane (asymmetric acrylamide compound represented by the following formula)

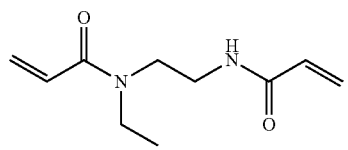

Symmetric (Meth)Acrylamide Compound
BAAE: Bisacrylamideethylene (symmetric acrylamide compound represented by the following formula)

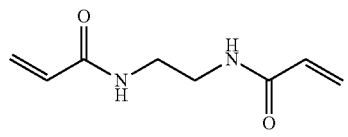

NEBAAP: N,N'-Diethyl-1,3-propylene-bisacrylamide (symmetric acrylamide compound represented by the following formula)

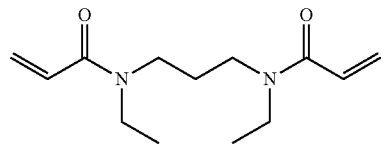 [SMILES: C=CC(=O)N(CC)CCCN(CC)C(=O)C=C]

Acid Group-Containing (Meth)Acrylic Polymerizable Monomer (c)
MDP: 10-Methacryloyloxydecyl dihydrogen phosphate
Hydrophilic Polymerizable Monomer (d)
DEAA: Diethylacrylamide
HEMA: 2-Hydroxyethylmethacrylate
GLM: 2,3-Dihydroxypropylmethacrylate
Hydrophobic Crosslinkable Polymerizable Monomer (e)
Bis-GMA: 2,2-Bis[4-(3-methacryloyloxy-2-hydroxypropoxy)phenyl]propane
UDMA: 2,2,4-Trimethylhexamethylenebis(2-carbamoyloxyethyl)dimethacrylate
NPGDMA: Neopentyl glycol dimethacrylate
Polymerization Initiator (g)
CQ: dl-Camphorquinone
BAPO: Bis(2,4,6-trimethylbenzoyl)phenylphosphineoxide
TMDPO: 2,4,6-Trimethylbenzoyldiphenylphosphineoxide
Polymerization Accelerator (h)
DABE: 4-(N,N-Dimethylamino)ethyl benzoate
DEPT: N,N-Di(2-hydroxyethyl)-p-toluidine
Filler
R972: Silica fine particles "Aerosil R-972" manufactured by Nippon Aerosil Co., Ltd.; average particle diameter: 16 nm
Ar380: Silica fine particles "Aerosil 380" manufactured by Nippon Aerosil Co., Ltd.; average particle diameter: 7 nm
Others
BHT: 2,6-Di-t-butyl-4-methylphenol (stabilizer (polymerization inhibitor))
TBHQ: tert-Butylhydroquinone (stabilizer (polymerization inhibitor))

Synthesis Example 1

Synthesis of TAC3

Diethylenetriamine (manufactured by Tokyo Chemical Industry Co., Ltd.; 15.5 g, 0.15 mol), triethylamine (75.9 g, 0.75 mol), p-methoxyphenol (3.7 mg, 0.03 mmol), and 250 mL of dichloromethane were put into a 1-liter four-neck flask, stirred, and cooled to an internal temperature of 2° C. One-hundred milliliters of a dichloromethane solution of acrylic acid chloride (67.9 g, 0.75 mol) was then added dropwise over the course of 2 hours at 5° C. or lower. After the dropwise addition of the solution, the resulting mixture was stirred for 24 hours under room temperature conditions. The reaction solution was filtered, and insoluble matters were washed with a 1:1 solution of ethyl acetate and methanol. The filtrate was concentrated under reduced pressure at 35° C. or lower. The concentrated residue thus obtained was purified by silica gel column chromatography (developing solvent: a 6:1 mixture of ethyl acetate and methanol). After the column purification, the solvent was removed under reduced pressure using a rotary evaporator, and a white solid was obtained. The solid was subjected to LC/MS analysis and $^1$H-NMR measurement. It was determined from the locations and integrals of signals that the white solid was a target compound. The weight yield was 7.4 g, and the percentage yield was 18.5%.

MS m/z: 266 (M+H)$^+$ $^1$H-NMR (270 MHz D$_2$O): δ 3.41 (t, 4H), 3.57 (m, 4H), 5.63 (m, 3H), 6.05 (m, 5H), 6.54 (m, 1H) (ppm)

Synthesis Example 2

Synthesis of TAC4

Triethylenetetramine (manufactured by Tokyo Chemical Industry Co., Ltd.; 21.9 g, 0.15 mol), triethylamine (75.9 g, 0.75 mol), p-methoxyphenol (3.7 mg, 0.03 mmol), and 250 mL of dichloromethane were put into a 1-liter four-neck flask, stirred, and cooled to an internal temperature of 2° C. One-hundred milliliters of a dichloromethane solution of acrylic acid chloride (67.9 g, 0.75 mol) was then added dropwise over the course of 2 hours at 5° C. or lower. After the dropwise addition of the solution, the resulting mixture was stirred for 24 hours under room temperature conditions. The reaction solution was filtered, and insoluble matters were washed with dichloromethane. The filtrate was concentrated under reduced pressure at 35° C. or lower. The concentrated residue thus obtained was purified by silica gel column chromatography (developing solvent: a 4:1 mixture of ethyl acetate and methanol). After the column purification, the solvent was removed under reduced pressure using a rotary evaporator, and a white solid was obtained. The solid was subjected to LC/MS analysis and $^1$H-NMR measurement. It was determined from the locations and integrals of signals that the white solid was a target compound. The weight yield was 12.7 g, and the percentage yield was 23.3%.

MS m/z: 363 (M+H)$^+$ $^1$H-NMR (270 MHz D$_2$O): δ 3.37 (m, 6H), 3.57 (m, 6H), 5.66 (m, 4H), 6.07 (m, 6H), 6.56 (m, 2H) (ppm)

Synthesis Example 3

Synthesis of TOT-BA

Diethylene glycol bis(3-aminopropyl)ether (manufactured by Tokyo Chemical Co., Ltd.; 33.0 g, 0.15 mol), triethylamine (30.4 g, 0.30 mol), p-methoxyphenol (3.7 mg, 0.03 mmol), and 250 mL of dichloromethane were put into a 1-liter four-neck flask, stirred, and cooled to an internal temperature of 2° C. One-hundred milliliters of a dichloromethane solution of acrylic acid chloride (27.2 g, 0.30 mol) was then added dropwise over the course of 2 hours at 5° C. or lower. After the dropwise addition of the solution, the resulting mixture was stirred for 24 hours under room temperature conditions. The reaction solution was filtered, and insoluble matters were washed with dichloromethane. The filtrate was concentrated under reduced pressure at 35° C. or lower. The concentrated residue thus obtained was purified by silica gel column chromatography (developing solvent: a 4:1 mixture of ethyl acetate and methanol). After the column purification, the solvent was removed under reduced pressure using a rotary evaporator, and a white solid was obtained. The solid was subjected to LC/MS analysis and $^1$H-NMR measurement. It was determined from the locations and integrals of signals that the white solid was a target compound. The weight yield was 17.3 g, and the percentage yield was 35.1%.

MS m/z: 329 (M+H)$^+$ $^1$H-NMR (270 MHz D$_2$O): δ 1.70 (tt, 4H), 3.25 (t, 4H), 3.46-3.60 (m, 12H), 5.62 (m, 2H), 6.10 (m, 2H), 6.15 (m, 2H) (ppm)

Synthesis Example 4

Synthesis of TEGDAA

Triethylene glycol (manufactured by Tokyo Chemical Industry Co., Ltd., 22.5 g, 0.15 mol), triethylamine (30.4 g, 0.30 mol), p-methoxyphenol (3.7 mg, 0.03 mmol), and 250 mL of dichloromethane were put into a 1-liter four-neck flask, stirred, and cooled to an internal temperature of 2° C. One-hundred milliliters of a dichloromethane solution of acrylic acid chloride (27.2 g, 0.30 mol) was then added dropwise over the course of 2 hours at 5° C. or lower. After the dropwise addition of the solution, the resulting mixture was stirred for 24 hours under room temperature conditions. The reaction solution was filtered, and insoluble matters were washed with dichloromethane. The filtrate was concentrated under reduced pressure at 35° C. or lower. The concentrated residue thus obtained was purified by silica gel column chromatography (developing solvent: a 4:1 mixture of ethyl acetate and methanol). After the column purification, the solvent was removed under reduced pressure using a rotary evaporator, and a white solid was obtained. The solid was subjected to LC/MS analysis and $^1$H-NMR measurement. It was determined from the locations and integrals of signals that the white solid was a target compound.

The weight yield was 14.9 g, and the percentage yield was 38.8%.

MS m/z: 257 (M+H)+

$^1$H-NMR (270 MHz CDCl$_3$): δ 3.52-3.56 (m, 4H), 3.59-3.62 (m, 8H), 5.62-5.65 (m, 2H), 6.13-6.19 (m, 2H), 6.27-6.31 (m, 2H), 6.43 (br, 2H) (ppm)

Synthesis Example 5

Synthesis of MAEA

Hydroxyethylacrylamide (manufactured by Kohjin Film & Chemicals Co., Ltd.; 172.7 g, 1.5 mol), triethylamine (167 g, 1.65 mol), p-methoxyphenol (38 mg, 0.3 mmol), and 1,500 mL of anhydrous tetrahydrofuran were put into a 10-liter four-neck flask, stirred, and cooled to an internal temperature of −10° C. Seven-hundred milliliters of an anhydrous tetrahydrofuran solution of methacrylic acid chloride (172.5 g, 1.65 mol) was then added dropwise over the course of 2 hours at 5° C. or lower. After the dropwise addition of the solution, the resulting mixture was stirred for 24 hours under room temperature conditions. The reaction solution was filtered, and insoluble matters were washed with ethyl acetate. The filtrate was concentrated under reduced pressure, and the residue was dissolved in ethyl acetate. The resulting solution was filtered with Celite to remove a small amount of insoluble matters, and the filtrate was washed with a mixture of saturated saline solution and purified water (1:1). The organic layer was dried over anhydrous sodium sulfate, and concentrated under reduced pressure at 35° C. or lower. The concentrated residue thus obtained was purified by silica gel column chromatography (developing solvent: ethyl acetate). After the column purification, the solvent was removed under reduced pressure using a rotary evaporator, and a pale yellow liquid was obtained. The liquid was subjected to LC-MS analysis and $^1$H-NMR measurement. It was determined from the locations and integrals of signals that the pale yellow liquid was a target compound. The weight yield was 201.2 g, and the percentage yield was 73.3%.

MS m/z: 184 (M+H)+

$^1$H-NMR (270 MHz CDCl$_3$): δ 1.94 (m, 3H), 3.62 (m, 2H), 4.28 (m, 2H), 5.58 (m, 1H), 5.66 (m, 1H), 6.08 (s, 1H), 6.10 (m, 1H), 6.11 (m, 1H), 6.28 (m, 1H) (ppm)

Synthesis Example 6

Synthesis of MAPA

3-Aminopropanol (Manufactured by Tokyo Chemical Industry; 23.9 g, 0.318 mol), and 400 mL of anhydrous tetrahydrofuran were put into a 1-liter four-neck flask, stirred, and cooled to an internal temperature of −10° C. Seventy milliliters of an anhydrous tetrahydrofuran solution of acrylic acid chloride (14.4 g, 0.159 mol) was then added dropwise over the course of 30 minutes at 5° C. or lower. After the dropwise addition of the solution, the resulting mixture was stirred for 1 hour under room temperature conditions. After the reaction, insoluble matters were filtered and removed, and the filtrate was concentrated under reduced pressure. This produced hydroxypropyl acrylamide as a pale yellow liquid.

The hydroxypropyl acrylamide (12.9 g, 0.1 mol) obtained by the procedure described above, 200 mL of anhydrous tetrahydrofuran, and triethylamine (15.2 g, 0.15 mol) were put into a 500-milliliter four-necked flask, stirred, and cooled to an internal temperature of −10° C. Fifty milliliters of an anhydrous tetrahydrofuran solution of methacrylic acid chloride (15.7 g, 0.15 mol) was then added dropwise over the course of 30 minutes at 5° C. or lower. After the dropwise addition of the solution, the resulting mixture was stirred for 3 hours under room temperature conditions. After the reaction, triethylamine hydrochloride was removed by filtration, and the filtrate was concentrated under reduced pressure. The concentrated residue was purified by silica gel column chromatography (developing solvent: ethyl acetate/hexane=2/1). After the column purification, the solvent was removed under reduced pressure using a rotary evaporator, and a white solid was obtained. The solid was subjected to LC-MS analysis and $^1$H-NMR measurement. It was determined from the locations and integrals of signals that the white solid was a target compound. The weight yield was 11.1 g, and the percentage yield was 56.3%.

MS m/z: 198 (M+H)+

$^1$H-NMR (270 MHz CDCl$_3$): δ 1.93 (m, 2H), 1.97 (m, 3H), 3.42 (m, 2H), 4.27 (m, 2H), 5.58 (m, 1H), 5.65 (m, 1H), 6.11 (s, 1H), 6.10 (m, 1H), 6.13 (m, 1H), 6.30 (m, 1H) (ppm)

Synthesis Example 7

Synthesis of MAEEA

DL-2-Amino-1-butanol (Manufactured by Tokyo Chemical Industry; 28.3 g, 0.318 mol), and 400 mL of anhydrous tetrahydrofuran were put into a 1-liter four-necked flask, stirred, and cooled to an internal temperature of −10° C. Seventy milliliters of an anhydrous tetrahydrofuran solution of acrylic acid chloride (14.4 g, 0.159 mol) was then added dropwise over the course of 30 minutes at 5° C. or lower. After the dropwise addition of the solution, the resulting mixture was stirred for 1 hour under room temperature conditions. After the reaction, insoluble matters were removed by filtration, and the filtrate was concentrated under reduced pressure. This produced N-(1-ethyl-(2-hydroxy)ethyl)acrylamide as a pale yellow liquid.

The N-(1-ethyl-(2-hydroxy)ethyl)acrylamide (14.3 g, 0.1 mol) obtained by the procedure described above, 200 mL of anhydrous tetrahydrofuran, and triethylamine (15.2 g, 0.15 mol) were put into a 500-milliliter four-necked flask, stirred, and cooled to an internal temperature of −10° C. Fifty milliliters of an anhydrous tetrahydrofuran solution of methacrylic acid chloride (15.7 g, 0.15 mol) was then added dropwise over the course of 30 minutes at 5° C. or lower. After the dropwise addition of the solution, the resulting mixture was stirred for 3 hours under room temperature conditions. After the reaction, triethylamine hydrochloride was removed by filtration, and the filtrate was concentrated under reduced pressure. The concentrated residue was purified by silica gel column chromatography (developing solvent: ethyl acetate/hexane=2/1). After the column purification, the solvent was removed under reduced pressure using a rotary evaporator, and a pale yellow liquid was obtained. The liquid was subjected to LC-MS analysis and $^1$H-NMR measurement. It was determined from the locations and integrals of signals that the pale yellow liquid was a target compound. The weight yield was 7.7 g, and the percentage yield was 36.3%.

MS m/z: 212 (M+H)+

$^1$H-NMR (270 MHz DMSO-d$_6$): δ 0.81 (m, 3H), 1.44 (m, 2H), 1.94 (m, 3H), 3.75 (m, 1H), 4.42 (m, 2H), 5.57 (m, 1H), 5.65 (m, 1H), 6.11 (m, 1H), 6.13 (m, 1H), 6.28 (m, 1H), 8.04 (s, 1H) (ppm)

Synthesis Example 8

Synthesis of MAEGA 2-(2-Aminoethoxy)ethanol (Manufactured by Tokyo Chemical Industry; 33.4 g, 0.318 mol), and 400 mL of anhydrous tetrahydrofuran were put into a 1-liter four-necked flask, stirred, and cooled to an internal temperature of −10° C. Seventy milliliters of an anhydrous tetrahydrofuran solution of acrylic acid chloride (14.4 g, 0.159 mol) was then added dropwise over the course of 30 minutes at 5° C. or lower. After the dropwise addition of the solution, the resulting mixture was stirred for 1 hour under room temperature conditions. After the reaction, insoluble matters were removed by filtration, and the filtrate was concentrated under reduced pressure. This produced N-(2-(2-hydroxyethoxy)ethyl)acrylamide as a pale yellow liquid.

The N-(2-(2-hydroxyethoxy)ethyl)acrylamide (15.9 g, 0.1 mol) obtained by the procedure described above, 200 mL of anhydrous tetrahydrofuran, and triethylamine (15.2 g, 0.15 mol) were put into a 500-milliliter four-necked flask, stirred, and cooled to an internal temperature of −10° C. Fifty milliliters of an anhydrous tetrahydrofuran solution of methacrylic acid chloride (15.7 g, 0.15 mol) was then added dropwise over the course of 30 minutes at 5° C. or lower. After the dropwise addition of the solution, the resulting mixture was stirred for 3 hours under room temperature conditions. After the reaction, triethylamine hydrochloride was removed by filtration, and the filtrate was concentrated under reduced pressure. The concentrated residue was purified by silica gel column chromatography (developing solvent: ethyl acetate/hexane=2/1). After the column purification, the solvent was removed under reduced pressure using a rotary evaporator, and a pale yellow liquid was obtained. The liquid was subjected to LC-MS analysis and $^1$H-NMR measurement. It was determined from the locations and integrals of signals that the pale yellow liquid thus obtained was a target compound. The weight yield was 10.4 g, and the percentage yield was 45.8%.

MS m/z: 228 (M+H)⁺

¹H-NMR (270 MHz DMSO-$d_6$): δ 1.93 (m, 3H), 3.28 (m, 2H), 3.43 (m, 2H), 3.49 (m, 2H), 4.34 (m, 2H), 5.59 (m, 1H), 5.63 (m, 1H), 6.09 (m, 1H), 6.12 (m, 1H), 6.30 (m, 1H), 8.17 (s, 1H) (ppm)

Synthesis Example 9

Synthesis of NEBAE

N-Ethylethylenediamine (manufactured by Koei Chemical Co., Ltd.; 200 g, 2.269 mol), triethylamine (688.9 g, 6.807 mol), and 4 L of chloroform were put into a 10-liter four-necked flask, stirred, and cooled to an internal temperature of −10° C. Acrylic acid chloride (616.1 g, 6.807 mol) was then added dropwise over the course of 1 hour at 10° C. or lower. After the dropwise addition of the solution, the resulting mixture was stirred for 1 hour under room temperature conditions. After the stirring was stopped, 4 L of water and 2 L of chloroform were added to the reaction solution for liquid-liquid extraction, and the water layer was further extracted with 2 L of chloroform. The chloroform layer was washed with 4 L of water, dried over sodium sulfate, and concentrated at 35° C. or lower under reduced pressure. The concentrated residue was purified by silica gel column chromatography (developing solvent: ethyl acetate/methanol=10/1). After the column purification, the solvent was removed under reduced pressure using a rotary evaporator, and a pale yellow liquid was obtained. The liquid was subjected to LC-MS analysis and ¹H-NMR measurement. It was determined from the locations and integrals of signals that the pale yellow liquid was a target compound. The weight yield was 127 g, and the percentage yield was 28.5%.

MS m/z: 197 (M+H)+

¹H-NMR (270 MHz CDCl₃): δ 1.20 (m, 3H), 3.42 (m, 2H), 5.54 (m, 2H), 5.60 (m, 2H), 5.59 (m, 1H), 5.74 (m, 1H), 6.11 (m, 1H), 6.18 (m, 1H), 6.40 (m, 1H), 6.61 (m, 1H), 7.15 (s, 1H) (ppm)

Synthesis Example 10

Synthesis of MAEM

2-Aminoethanol (Manufactured by Tokyo Chemical Industry; 19.4 g, 0.318 mol), and 400 mL of anhydrous tetrahydrofuran were put into a 1-liter four-necked flask, stirred, and cooled to an internal temperature of −10° C. Seventy milliliters of an anhydrous tetrahydrofuran solution of methacrylic acid chloride (16.6 g, 0.159 mol) was then added dropwise over the course of 30 minutes at 5° C. or lower. After the dropwise addition of the solution, the resulting mixture was stirred for 3 hours under room temperature conditions. After the reaction, insoluble matters were removed by filtration, and the filtrate was concentrated under reduced pressure. This produced hydroxyethyl methacrylamide as a pale yellow liquid.

The hydroxyethyl methacrylamide (12.9 g, 0.10 mol) obtained by the procedure described above, 200 mL of anhydrous tetrahydrofuran, and triethylamine (15.2 g, 0.15 mol) were put into a 500-milliliter four-necked flask, stirred, and cooled to an internal temperature of −10° C. Fifty milliliters of an anhydrous tetrahydrofuran solution of methacrylic acid chloride (15.7 g, 0.15 mol) was then added dropwise over the course of 30 minutes at 5° C. or lower. After the dropwise addition of the solution, the resulting mixture was stirred for 3 hours under room temperature conditions. After the reaction, triethylamine hydrochloride was removed by filtration, and the filtrate was concentrated under reduced pressure. The concentrated residue was purified by silica gel column chromatography (developing solvent: ethyl acetate). After the column purification, the solvent was removed under reduced pressure using a rotary evaporator, and a pale yellow liquid was obtained. The liquid was subjected to LC-MS analysis and ¹H-NMR measurement. It was determined from the locations and integrals of signals that the pale yellow liquid was a target compound. The weight yield was 10.8 g, and the percentage yield was 54.8%.

MS m/z: 198 (M+H)+

¹H-NMR (270 MHz CDCl₃): δ 1.92 (m, 3H), 1.94 (m, 3H), 3.65 (m, 2H), 4.27 (m, 2H), 5.34 (m, 1H), 5.58 (m, 1H), 5.68 (m, 1H), 6.11 (m, 1H), 6.29 (s, 1H) (ppm)

Synthesis Example 11

Synthesis of NEBAAP

Acrylic acid chloride (18.1 g, 0.2 mol) was weighed into a 1-liter three-neck flask, and 5 mg of hydroquinone monomethyl ether (MEHQ), and 500 mL of dehydrated acetonitrile were added. After stirring the mixture under a nitrogen atmosphere, the internal temperature of the system was brought to −10 to −5° C. with iced saline solution, and a dehydrated acetonitrile solution (100 mL) of N,N'-diethyl-1,3-propanediamine (manufactured by Aldrich; 26.1 g, 0.2 mol) was added dropwise over the course of 2 hours. After the dropwise addition, the mixture was stirred overnight under room temperature conditions. After the reaction, the precipitate was removed by filtration, and washed twice with acetonitrile (100 mL). The filtrate was then concentrated under reduced pressure using an evaporator, and a yellow liquid-state concentrated residue was obtained. The liquid residue was dissolved in dichloromethane, followed by washing with 0.1 M HCl, a 5% sodium bicarbonate aqueous solution, and water. After drying over anhydrous sodium sulfate, the solvent was removed under reduced pressure using an evaporator, and a yellow liquid-state concentrated residue was obtained. It was determined from the locations and integrals of signals that the yellow liquid was a target compound. The weight yield was 13.4 g, and the percentage yield was 56.0%.

MS m/z: 239 (M+H)⁺

¹H-NMR (270 MHz CDCl₃): δ 1.10-1.24 (m, 6H), 1.78-1.91 (m, 2H), 3.34-3.60 (m, 8H), 5.61-5.78 (m, 2H), 6.30-6.67 (2m, 4H) (ppm)

Example 1 and Comparative Example 1

Application of Dental Adhesive to One-Step Adhesive System (One-Part Bonding Material)

One-part bonding materials having the compositions shown in Tables 1 to 3 were prepared using the materials given in the above-described synthesis examples and elsewhere. The unit of the values presented for the components listed in the tables is part by weight. The content of Examples and Comparative Examples, and the evaluation method used in Examples and Comparative Examples are as follows.

Examples 1-1 to 1-3

One-part bonding materials (compositions) containing polymerizable monomers TAC3, MAEA, MDP, DEAA, and Bis-GMA in the amounts shown in Table 1 were used to examine initial bond strength and bond durability to dentin according to the tensile bond strength measurement method described below (the bond strength test method and the bond durability test method of the Ultradent's shear bond test (ISO 29022: 2013; notched-edge shear bond strength test), with and without phosphoric acid etching. Here, TAC3 corresponds to the (meth)acrylamide compound (a), MAEA corresponds to the asymmetric acrylamide-methacrylic acid ester compound (b), MDP corresponds to the acid group-containing (meth)acrylic polymerizable monomer (c), DEAA corresponds to the hydrophilic polymerizable monomer (d), and Bis-GMA corresponds to the hydrophobic crosslinkable polymerizable monomer (e). (The same test methods were used to examine initial bond strength and bond durability in other Examples and in Comparative Examples.)

Examples 1-4 to 1-6

One-part bonding materials (compositions) containing polymerizable monomers TAC4, MAEA, MDP, DEAA, and Bis-GMA in the amounts shown in Table 1 were used to examine initial bond strength and bond durability to dentin, with and without phosphoric acid etching. Here, TAC4 corresponds to the (meth)acrylamide compound (a), MAEA corresponds to the asymmetric acrylamide-methacrylic acid ester compound (b), MDP corresponds to the acid group-containing (meth)acrylic polymerizable monomer (c), DEAA corresponds to the hydrophilic polymerizable monomer (d), and Bis-GMA corresponds to the hydrophobic crosslinkable polymerizable monomer (e).

Examples 1-7 to 1-8

Initial bond strength and bond durability to dentin were examined with and without phosphoric acid etching in the same manner as in Example 1-4, except that the hydrophilic polymerizable monomer (d) in the one-part bonding material was changed as shown in Table 1.

Examples 1-9 to 1-11

Initial bond strength and bond durability to dentin were examined with and without phosphoric acid etching in the same manner as in Example 1-5, except that the MAEA in the one-part bonding material was replaced with MAPA, MAEEA, or MAEGA.

Example 1-12

Initial bond strength and bond durability to dentin were examined with and without phosphoric acid etching in the same manner as in Example 1-7, except that the Bis-GMA in the one-part bonding material was used in the amount shown in Table 1, and that NaF was used as a fluorine ion-releasing component in the amount shown in Table 1.

Example 1-13

Initial bond strength and bond durability to dentin were examined with and without phosphoric acid etching in the same manner as in Example 1-7, except that the Bis-GMA in the one-part bonding material was replaced with UDMA, and used in the amount shown in Table 1.

Example 1-14

Initial bond strength and bond durability to dentin were examined with and without phosphoric acid etching in the same manner as in Example 1-7, except that the ethanol in the one-part bonding material was replaced with acetone, and that Bis-GMA was used in the amount shown in Table 2.

Examples 1-15 to 1-18

One-part bonding materials (compositions) containing polymerizable monomers TOT-BA, MAEA, MDP, DEAA, and Bis-GMA in the amounts shown in Table 2 were used to examine initial bond strength and bond durability to dentin, with and without phosphoric acid etching. Here, TOT-BA corresponds to the (meth)acrylamide compound (a), MAEA corresponds to the asymmetric acrylamide-methacrylic acid ester compound (b), MDP corresponds to the acid group-containing (meth)acrylic polymerizable monomer (c), DEAA corresponds to the hydrophilic polymerizable monomer (d), and Bis-GMA corresponds to the hydrophobic crosslinkable polymerizable monomer (e).

Example 1-19

Initial bond strength and bond durability to dentin were examined with and without phosphoric acid etching in the same manner as in Example 1-12, except that DEPT, corresponding to the polymerization accelerator, contained in the one-part bonding material was used in the amount shown in Table 2.

Example 1-20

Initial bond strength and bond durability to dentin were examined with and without phosphoric acid etching in the same manner as in Example 1-19, except that the one-part bonding material did not contain NaF, and that the BAPO corresponding to the polymerization initiator was replaced with TMDPO, and used in the amount shown in Table 2.

Examples 1-21 to 1-24

One-part bonding materials (compositions) containing polymerizable monomers TEGDAA, MAEA, MDP, DEAA, and Bis-GMA in the amounts shown in Table 2 were used to examine initial bond strength and bond durability to dentin, with and without phosphoric acid etching. Here, TEGDAA corresponds to the (meth)acrylamide compound (a), MAEA corresponds to the asymmetric acrylamide-methacrylic acid ester compound (b), MDP corresponds to the acid group-containing (meth)acrylic polymerizable monomer (c), DEAA corresponds to the hydrophilic polymerizable monomer (d), and Bis-GMA corresponds to the hydrophobic crosslinkable polymerizable monomer (e).

Comparative Example 1-1

A one-part bonding material (composition) containing polymerizable monomers BAAE, MDP, and Bis-GMA in the amounts shown in Table 3 was used to examine initial bond strength and bond durability to dentin, with and without phosphoric acid etching. Here, BAAE corresponds to the symmetric acrylamide compound, MDP corresponds to the acid group-containing (meth)acrylic polymerizable monomer (c), and Bis-GMA corresponds to the hydrophobic crosslinkable polymerizable monomer (e).

Comparative Example 1-2

A one-part bonding materials (compositions) containing polymerizable monomers NEBAAP, MAEA, MDP, DEAA, and Bis-GMA in the amounts shown in Table 3 was used to examine initial bond strength and bond durability to dentin, with and without phosphoric acid etching. Here, NEBAAP corresponds to the symmetric acrylamide compound, MAEA corresponds to the asymmetric acrylamide-methacrylic acid ester compound (b), MDP corresponds to the acid group-containing (meth)acrylic polymerizable monomer (c), DEAA corresponds to the hydrophilic polymerizable monomer (d), and Bis-GMA corresponds to the hydrophobic crosslinkable polymerizable monomer (e).

Comparative Example 1-3

Initial bond strength and bond durability to dentin were examined with and without phosphoric acid etching in the same manner as in Comparative Example 1-2, except that the MAEA in the one-part bonding material was replaced with MAEM corresponding to the symmetric methacrylamide-methacrylic acid ester compound, and that NEBAAP was replaced with NEBAE corresponding to the asymmetric (meth)acrylamide compound.

Comparative Example 1-4

Initial bond strength and bond durability to dentin were examined with and without phosphoric acid etching in the same manner as in Comparative Example 1-1, except that the BAAE in the one-part bonding material was replaced with NEBAE corresponding to the asymmetric (meth)acrylamide compound.

Comparative Examples 1-5 to 1-6

One-part bonding materials (compositions) containing polymerizable monomers MAEM, MDP, DEAA, and Bis-GMA in the amounts shown in Table 3 were used to examine initial bond strength and bond durability to dentin, with and without phosphoric acid etching. Here, MAEM corresponds to the symmetric methacrylamide-methacrylic acid ester compound, MDP corresponds to the acid group-containing (meth)acrylic polymerizable monomer (c), DEAA corresponds to the hydrophilic polymerizable monomer (d), and Bis-GMA corresponds to the hydrophobic crosslinkable polymerizable monomer (e).

Measurement of Tensile Bond Strength to Dentin Untreated by Phosphoric Acid Etching The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

The one-part bonding materials prepared in Examples and Comparative Examples were applied within the circular hole with an applicator brush (manufactured by Kuraray Noritake Dental Inc.; Model No. 241-024), and rubbed for 10 seconds, after which the applied one-part bonding material was dried by subjecting its surface to air-blowing until the bonding material lost its flowability. Subsequently, the applied one-part bonding material was cured by 10-second light irradiation with a dental visible light irradiation device (manufactured by Morita Corporation under the trade name "PenCure 2000").

To the surface of the obtained cured product of the one-part bonding material was applied a dental filling composite resin (manufactured by Kuraray Noritake Dental Inc. under the trade name "CLEARFIL AP-X" (registered trademark)), and the resin was covered with a release film (made of polyester). Next, a glass slide was placed on and pressed against the release film to flatten the surface of the applied composite resin. Subsequently, the composite resin was cured by subjecting the resin to 20-second light irradiation through the release film using the irradiation device "PenCure 2000".

Using a commercially-available dental resin cement (manufactured by Kuraray Noritake Dental Inc. under the trade name "PANAVIA 21"), a cylindrical stainless steel rod (with a diameter of 7 mm and a length of 2.5 cm) was bonded at its one end face (circular end face) to the surface of the obtained cured product of the dental filling composite resin. After the bonding, the sample was allowed to stand at room temperature for 30 minutes, after which the sample was immersed in distilled water. A total of 16 enamel samples and a total of 16 dentin samples were prepared for the bond test, and these samples in water were allowed to stand for 24 hours in a thermostat set at 37° C. Immediately after the 24-hour standing, 8 of the 16 samples were measured for bond strength to evaluate the initial bond strength. For the evaluation of the bond durability of the remaining 8 samples, these samples were measured for bond strength after being subjected to 4,000 cycles of a temperature cycling test, in which a cycle of alternately immersing the samples in 4° C. cold water for 1 minute and in 60° C. hot water for 1 minute was repeated.

The tensile bond strength of the above bond test samples was measured using a universal testing machine (manufactured by Shimadzu Corporation) with a crosshead speed set at 2 mm/min. The average of the measured values of these samples was used as the value of tensile bond strength.

Measurement of Tensile Bond Strength to Dentin Treated by Phosphoric Acid Etching The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing.

A dental phosphoric acid etching material (manufactured by Kuraray Noritake Dental Inc. under the trade name K-Etchant Syringe) was applied to dentin by slowly squeezing out the gel onto the dried smooth surface. The sample was then allowed to stand for 10 seconds, and washed and dried. To the dried smooth surface was attached an about 150-μm-thick adhesive tape having a circular hole of 3-mm diameter, so that an adhesive area was defined. The samples were then measured for tensile bond strength to dentin treated by phosphoric acid etching, in the same manner as for the measurement of tensile bond strength to dentin untreated by phosphoric acid etching treatment.

TABLE 1

| Components (parts by weight) | | Ex. 1-1 | Ex. 1-2 | Ex. 1-3 | Ex. 1-4 | Ex. 1-5 | Ex. 1-6 | Ex. 1-7 | Ex. 1-8 | Ex. 1-9 | Ex. 1-10 | Ex. 1-11 | Ex. 1-12 | Ex. 1-13 |
|---|---|---|---|---|---|---|---|---|---|---|---|---|---|---|
| (Meth)acrylamide compound (a) | TAC3 | 2 | 5 | 10 | — | — | — | — | — | — | — | — | — | — |
| | TAC4 | — | — | — | 2 | 5 | 10 | 2 | 2 | 5 | 5 | 5 | 2 | 2 |
| Asymmetric acrylamide- methacrylic acid ester compound (b) | MAEA | 18 | 15 | 10 | 18 | 15 | 10 | 18 | 18 | — | — | — | 18 | 18 |
| | MAPA | — | — | — | — | — | — | — | — | — | 15 | — | — | — |
| | MAEEA | — | — | — | — | — | — | — | — | 15 | — | — | — | — |
| | MAEGA | — | — | — | — | — | — | — | — | — | — | 15 | — | — |
| Acid group-containing (meth)acrylic polymerizable monomer (c) | MDP | 10 | 10 | 10 | 10 | 10 | 10 | 10 | 10 | 10 | 10 | 10 | 10 | 10 |
| Hydrophilic polymerizable monomer (d) | DEAA | 20 | 20 | 20 | 20 | 20 | 20 | 10 | 10 | 20 | 20 | 20 | 10 | 10 |
| | HEMA | — | — | — | — | — | — | 10 | — | — | — | — | 10 | 10 |
| | GLM | — | — | — | — | — | — | — | 10 | — | — | — | — | — |
| Hydrophobic polymerizable monomer (e) | Bis-GMA | 20 | 20 | 20 | 20 | 20 | 20 | 20 | 20 | 20 | 20 | 20 | 30 | — |
| | UDMA | — | — | — | — | — | — | — | — | — | — | — | — | 40 |
| Solvent (f) Water | Distilled water | 15 | 15 | 15 | 15 | 15 | 15 | 15 | 15 | 15 | 15 | 15 | 15 | 15 |
| Organic solvent | Ethanol | 15 | 15 | 15 | 15 | 15 | 15 | 15 | 15 | 15 | 15 | 15 | 15 | 15 |
| Polymerization initiator (g) | BAPO | 0.5 | 0.5 | 0.5 | 0.5 | 0.5 | 0.5 | 0.5 | 0.5 | 0.5 | 0.5 | 0.5 | 0.5 | 0.5 |
| | CQ | 2 | 2 | 2 | 2 | 2 | 2 | 2 | 2 | 2 | 2 | 2 | 2 | 2 |
| Polymerization accelerator (h) | DABE | 1 | 1 | 1 | 1 | 1 | 1 | 1 | 1 | 1 | 1 | 1 | 1 | 1 |
| | DEPT | 0.5 | 0.5 | 0.5 | 0.5 | 0.5 | 0.5 | 0.5 | 0.5 | 0.5 | 0.5 | 0.5 | 0.5 | 0.5 |
| Polymerization inhibitor | BHT | 0.05 | 0.05 | 0.05 | 0.05 | 0.05 | 0.05 | 0.05 | 0.05 | 0.05 | 0.05 | 0.05 | 0.05 | 0.05 |
| Fluorine ion-releasing component | NaF | — | — | — | — | — | — | — | — | — | — | — | 0.05 | — |
| Filler (i) | R972 | 7 | 7 | 7 | 7 | 7 | 7 | 7 | 7 | 7 | 7 | 7 | 7 | 7 |
| Tensile bond strength (MPa) Without phosphoric acid etching (dentin) | Initial bond strength | 20 | 21 | 20 | 22 | 23 | 21 | 23 | 21 | 21 | 20 | 22 | 23 | 20 |
| | Bond durability | 17 | 20 | 19 | 21 | 22 | 19 | 21 | 18 | 18 | 17 | 20 | 21 | 17 |
| With phosphoric acid etching (dentin) | Initial bond strength | 23 | 22 | 23 | 24 | 25 | 25 | 26 | 25 | 23 | 22 | 24 | 26 | 22 |
| | Bond durability | 21 | 21 | 22 | 22 | 24 | 23 | 24 | 23 | 21 | 20 | 22 | 24 | 20 |

TABLE 2

| Components (parts by weight) | | Ex. 1-14 | Ex. 1-15 | Ex. 1-16 | Ex. 1-17 | Ex. 1-18 | Ex. 1-19 | Ex. 1-20 | Ex. 1-21 | Ex. 1-22 | Ex. 1-23 | Ex. 1-24 |
|---|---|---|---|---|---|---|---|---|---|---|---|---|
| (Meth)acrylamide compound (a) | TAC4 | 2 | — | — | — | — | 2 | 2 | — | — | — | — |
| | TOT-BA | — | 2 | 5 | 15 | 18 | — | — | — | — | — | — |
| | TEGDAA | — | — | — | — | — | — | — | 2 | 5 | 15 | 18 |
| Asymmetric acrylamide- methacrylic acid ester compound (b) | MAEA | 18 | 18 | 15 | 5 | 2 | 18 | 18 | 18 | 15 | 5 | 2 |
| Acid group-containing (meth)acrylic polymerizable monomer (c) | MDP | 10 | 10 | 10 | 10 | 10 | 10 | 10 | 10 | 10 | 10 | 10 |
| Hydrophilic polymerizable monomer (d) | DEAA | 10 | 20 | 20 | 20 | 20 | 10 | 10 | 20 | 20 | 20 | 20 |
| | HEMA | 10 | — | — | 10 | 10 | — | — | — | — | — | — |
| Hydrophobic polymerizable monomer (e) | Bis-GMA | 35 | 20 | 20 | 20 | 20 | 30 | 30 | 20 | 20 | 20 | 20 |
| Solvent (f) Water | Distilled water | 15 | 15 | 15 | 15 | 15 | 15 | 15 | 15 | 15 | 15 | 15 |
| Organic solvent | Ethanol | — | 15 | 15 | 15 | 15 | 15 | 15 | 15 | 15 | 15 | 15 |
| | Acetone | 15 | — | — | — | — | — | — | — | — | — | — |
| Polymerization initiator (g) | BAPO | 0.5 | 0.5 | 0.5 | 0.5 | 0.5 | 0.5 | — | 0.5 | 0.5 | 0.5 | 0.5 |
| | TMDPO | — | — | — | — | — | — | 2 | — | — | — | — |
| | CQ | 2 | 2 | 2 | 2 | 2 | 2 | 2 | 2 | 2 | 2 | 2 |
| Polymerization accelerator (h) | DABE | 1 | 1 | 1 | 1 | 1 | 1 | 1 | 1 | 1 | 1 | 1 |
| | DEPT | 0.5 | 0.5 | 0.5 | 0.5 | 0.5 | 1.5 | 1.5 | 0.5 | 0.5 | 0.5 | 0.5 |
| Polymerization inhibitor | BHT | 0.05 | 0.05 | 0.05 | 0.05 | 0.05 | 0.05 | 0.05 | 0.05 | 0.05 | 0.05 | 0.05 |
| Fluorine ion-releasing component | NaF | — | — | — | — | — | 0.05 | — | — | — | — | — |
| Filler (i) | R972 | 7 | 7 | 7 | 7 | 7 | 7 | 7 | 7 | 7 | 7 | 7 |
| Tensile bond strength (MPa) Without phosphoric acid etching (dentin) | Initial bond strength | 21 | 21 | 23 | 22 | 22 | 23 | 21 | 21 | 21 | 22 | 23 |
| | Bond durability | 18 | 20 | 22 | 20 | 21 | 21 | 19 | 17 | 18 | 17 | 18 |
| With phosphoric acid etching (dentin) | Initial bond strength | 23 | 23 | 24 | 23 | 24 | 23 | 23 | 22 | 22 | 24 | 23 |
| | Bond durability | 21 | 20 | 22 | 22 | 22 | 20 | 20 | 20 | 22 | 21 | 21 |

TABLE 3

| Components (parts by weight) | | Com. Ex. 1-1 | Com. Ex. 1-2 | Com. Ex. 1-3 | Com. Ex. 1-4 | Com. Ex. 1-5 | Com. Ex. 1-6 |
|---|---|---|---|---|---|---|---|
| Asymmetric acrylamide-methacrylic acid ester compound (b) | MAEA | — | 10 | — | — | — | — |
| Symmetric methacrylamide-methacrylic acid ester compound | MAEM | — | — | 10 | — | 25 | 15 |
| Asymmetric acrylamide compound | NEBAE | — | — | 10 | 30 | — | — |
| Symmetric acrylamide compound | BAAE | 30 | — | — | — | — | — |
| | NEBAAP | — | 10 | — | — | — | — |
| Acid group-containing (meth)acrylic polymerizable monomer (c) | MDP | 10 | 10 | 10 | 10 | 10 | 10 |
| Hydrophilic polymerizable monomer (d) | DEAA | — | 10 | 10 | — | 5 | 15 |
| Hydrophobic polymerizable monomer (e) | Bis-GMA | 30 | 30 | 30 | 30 | 30 | 30 |
| Solvent (f) Water | Distilled water | 15 | 15 | 15 | 15 | 15 | 15 |
| Organic solvent | Ethanol | 15 | 15 | 15 | 15 | 15 | 15 |
| Polymerization initiator (g) | BAPO | 0.5 | 0.5 | 0.5 | 0.5 | 0.5 | 0.5 |
| | CQ | 2 | 2 | 2 | 2 | 2 | 2 |
| Polymerization accelerator (h) | DABE | 1 | 1 | 1 | 1 | 1 | 1 |
| | DEPT | 0.5 | 0.5 | 0.5 | 0.5 | 0.5 | 0.5 |
| Polymerization inhibitor | BHT | 0.05 | 0.05 | 0.05 | 0.05 | 0.05 | 0.05 |
| Filler (i) | R972 | 7 | 7 | 7 | 7 | 7 | 7 |
| Tensile bond strength (MPa) | Without phosphoric acid etching (dentin) | Initial bond strength | 10 | 18 | 16 | 18 | 14 | 15 |
| | | Bond durability | 6 | 14 | 12 | 13 | 9 | 11 |
| | With phosphoric acid etching (dentin) | Initial bond strength | 8 | 11 | 11 | 12 | 10 | 12 |
| | | Bond durability | 3 | 7 | 5 | 5 | 6 | 6 |

As shown in Tables 1 and 2, the one-part bonging materials (Examples 1-1 to 1-24) as examples of the dental adhesive according to the present invention exhibited an initial bond strength of 20 MPa or more, and a bond durability of 17 MPa or more to dentin untreated by phosphoric acid etching. The initial bond strength, and the bond durability were 20 MPa or more to dentin treated by phosphoric acid etching. On the other hand, as shown in Table 3, the bonding material (Comparative Example 1-1) that contained the symmetric acrylamide compound instead of the (meth)acrylamide compound (a), and that did not contain the asymmetric acrylamide-methacrylic acid ester compound (b) had poor compatibility with BAAE, and the composition was inhomogeneous. The bond durability to dentin treated by phosphoric acid etching was 3 MPa. The bonding material (Comparative Example 1-2) that contained the asymmetric acrylamide-methacrylic acid ester compound (b), and that contained the symmetric acrylamide compound instead of the (meth)acrylamide compound (a) had a bond durability of 7 MPa to dentin treated by phosphoric acid etching. The bonding material (Comparative Example 1-3) that contained the asymmetric acrylamide compound instead of the (meth)acrylamide compound (a), and that contained the symmetric acrylamide-methacrylic acid ester compound instead of the asymmetric acrylamide-methacrylic acid ester compound (b) had a bond durability of 5 MPa to dentin treated by phosphoric acid etching. The bonding material (Comparative Example 1-4) that contained the asymmetric acrylamide compound NEBAE instead of the (meth)acrylamide compound (a), and that did not contain the asymmetric acrylamide-methacrylic acid ester compound (b) had a bond durability of 5 MPa to dentin treated by phosphoric acid etching. The bond durability to dentin treated by phosphoric acid etching was 6 MPa in the one-part bonding materials (Comparative Examples 1-5 and 1-6) that contained the symmetric methacrylamide-methacrylic acid ester compound MAEM instead of the asymmetric acrylamide-methacrylic acid ester compound (b), and that did not contain the (meth)acrylamide compound (a). The one-part bonding materials of Examples all had better initial bond strengths than any of the one-part bonding materials of Comparative Examples, regardless of the presence or absence of phosphoric acid etching.

Example 2 and Comparative Example 2

Application of Dental Adhesive to Two-Step Adhesive System (Primer)

Primers having the compositions shown in Table 4 were prepared using the materials given in the above-described synthesis examples and elsewhere. Bonding materials having the composition shown in Table 5 were also prepared. The unit of the values presented for the components listed in the tables is part by weight. The content of Examples and Comparative Examples, and the evaluation method used in Examples and Comparative Examples are as follows.

Example 2-1

The bonding material of Table 5 was used with a primer containing polymerizable monomers TAC3, MAEA, MDP, and DEAA and HEMA in the amounts shown in Table 4, and the initial bond strength and the bond durability to dentin were examined according to the tensile bond strength measurement method described below (the bond strength test method and the bond durability test method of the Ultradent's shear bond test), with and without phosphoric acid etching. Here, TAC3 corresponds to the (meth)acrylamide compound (a), MAEA corresponds to the asymmetric acrylamide-methacrylic acid ester compound (b), MDP corresponds to the acid group-containing (meth)acrylic polymerizable monomer (c), and DEAA and HEMA correspond to the hydrophilic polymerizable monomer (d). (The same test methods were used to examine initial bond strength and bond durability in other Examples and in Comparative Example, using the primer with the bonding material of Table 5.)

Example 2-2

Initial bond strength and bond durability to dentin were examined with and without phosphoric acid etching in the same manner as in Example 2-1, except that the TAC3 in the primer was replaced with TAC4, and used in the amount shown in Table 4.

Example 2-3

Initial bond strength and bond durability to dentin were examined with and without phosphoric acid etching in the same manner as in Example 2-1, except that the TAC3 in the primer was replaced with TOT-BA, and used in the amount shown in Table 4, and that MAEA was used in the amount shown in Table 4.

Example 2-4

Initial bond strength and bond durability to dentin were examined with and without phosphoric acid etching in the same manner as in Example 2-2, except that the hydrophilic polymerizable monomer (d) in the primer was changed as shown in Table 4.

Example 2-5

Initial bond strength and bond durability to dentin were examined with and without phosphoric acid etching in the same manner as in Example 2-2, except that the MAEA in the primer was used in the amount shown in Table 4.

Examples 2-6 to 2-8

Initial bond strength and bond durability to dentin were examined with and without phosphoric acid etching in the same manner as in Example 2-2, except that the MAEA in the primer was replaced with MAPA, MAEEA, or MAEGA.

Example 2-9

Initial bond strength and bond durability to dentin were examined with and without phosphoric acid etching in the same manner as in Example 2-3, except that the TOT-BA in the primer was replaced with TEGDAA, and used in the amount shown in Table 4.

Comparative Example 2-1

Initial bond strength and bond durability to dentin were examined with and without phosphoric acid etching using a primer that contained polymerizable monomers MAEGA, BAAE, MDP, and DEAA and HEMA in the amounts shown in Table 4, but did not contain the (meth)acrylamide compound (a). Here, MAEGA corresponds to the asymmetric acrylamide-methacrylic acid ester compound (b), BAAE corresponds to the symmetric acrylamide compound, MDP corresponds to the acid group-containing (meth)acrylic polymerizable monomer (c), and DEAA and HEMA correspond to the hydrophilic polymerizable monomer (d).

Measurement of Tensile Bond Strength to Dentin Untreated by Phosphoric Acid Etching The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

The primers prepared in Examples and Comparative Example were applied within the circular hole with an applicator brush (manufactured by Kuraray Noritake Dental Inc.; Model No. 241-024), and rubbed for 20 seconds, after which the applied primer was dried by subjecting its surface to air-blowing until the primer lost its flowability. The bonding material of the composition shown in Table 5 was then applied over the dry, coated primer on the tooth surface. Subsequently, the applied primer and bonding material was cured by 10-second light irradiation with a dental LED light irradiation device (manufactured by Morita Corporation under the trade name "PenCure 2000").

To the surface of the obtained cured product of the primer and the bonding material was applied a dental filling composite resin (manufactured by Kuraray Noritake Dental Inc. under the trade name "CLEARFIL AP-X" (registered trademark)), and the resin was covered with a release film (made of polyester). Next, a glass slide was placed on and pressed against the release film to flatten the surface of the applied composite resin. Subsequently, the composite resin was cured by subjecting the resin to 20-second light irradiation through the release film using the irradiation device "PenCure 2000".

Using a commercially-available dental resin cement (manufactured by Kuraray Noritake Dental Inc. under the trade name "PANAVIA 21"), a cylindrical stainless steel rod (with a diameter of 7 mm and a length of 2.5 cm) was bonded at its one end face (circular end face) to the surface of the obtained cured product of the dental filling composite resin. After the bonding, the sample was allowed to stand at room temperature for 30 minutes, after which the sample was immersed in distilled water. A total of 16 enamel samples and a total of 16 dentin samples were prepared for the bond test, and these samples were allowed to stand for 24 hours in a thermostat set at 37° C. Immediately after the 24-hour standing, 8 of the 16 samples were measured for bond strength to evaluate the initial bond strength. For the evaluation of the bond durability of the remaining 8 samples, these samples were measured for bond strength after being subjected to 4,000 cycles of a temperature cycling test, in which a cycle of alternately immersing the samples in 4° C. cold water for 1 minute and in 60° C. hot water for 1 minute was repeated.

The tensile bond strength of the above bond test samples was measured using a universal testing machine (manufactured by Shimadzu Corporation) with a crosshead speed set at 2 mm/min. The average of the measured values of these samples was used as the value of tensile bond strength.

Measurement of Tensile Bond Strength to Dentin Treated by Phosphoric Acid Etching The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing.

A dental phosphoric acid etching material (manufactured by Kuraray Noritake Dental Inc. under the trade name K-Etchant Syringe) was applied to dentin by slowly squeezing out the gel onto the dried smooth surface. The sample was then allowed to stand for 10 seconds, and washed and dried. To the dried smooth surface was attached an about 150-μm-thick adhesive tape having a circular hole of 3-mm diameter, so that an adhesive area was defined. The samples were then measured for tensile bond strength to dentin treated by phosphoric acid etching, in the same manner as for the measurement of tensile bond strength to dentin untreated by phosphoric acid etching.

symmetric acrylamide compound instead of the (meth)acrylamide compound (a) had a bond durability of less than 10 MPa to dentin treated by phosphoric acid etching.

INDUSTRIAL APPLICABILITY

The dental adhesive according to the present invention can be used in various dental adhesive materials such as a primer and a bonding material, and can be particularly suitably used as a one-part bonding material.

The invention claimed is:
1. A dental adhesive comprising:
a (meth)acrylamide compound (a);
an asymmetric acrylamide-methacrylic acid ester compound (b); and
an acid group-containing (meth)acrylic polymerizable monomer (c),

TABLE 4

| Components (parts by weight) | | Ex. 2-1 | Ex. 2-2 | Ex. 2-3 | Ex. 2-4 | Ex. 2-5 | Ex. 2-6 | Ex. 2-7 | Ex. 2-8 | Ex. 2-9 | Com. Ex. 2-1 |
|---|---|---|---|---|---|---|---|---|---|---|---|
| (Meth)acrylamide compound (a) | TAC3 | 2 | — | — | — | — | — | — | — | — | — |
| | TAC4 | — | 2 | — | 2 | 2 | 2 | 2 | 2 | — | — |
| | TOT-BA | — | — | 5 | — | — | — | — | — | — | — |
| | TEGDAA | — | — | — | — | — | — | — | — | 5 | — |
| Asymmetric acrylamide- | MAEA | 8 | 8 | 5 | 8 | 15 | — | — | — | 5 | — |
| methacrylic acid | MAPA | — | — | — | — | — | 8 | — | — | — | — |
| ester compound (b) | MAEEA | — | — | — | — | — | — | 8 | — | — | — |
| | MAEGA | — | — | — | — | — | — | — | 8 | — | 5 |
| Symmetric acrylamide compound | BAAE | — | — | — | — | — | — | — | — | — | 30 |
| Acid group-containing (meth)acrylic polymerizable monomer (c) | MDP | 15 | 15 | 15 | 15 | 15 | 15 | 15 | 15 | 15 | 15 |
| Hydrophilic polymerizable monomer (d) | DEAA | 15 | 15 | 15 | 30 | 15 | 15 | 15 | 15 | 15 | 15 |
| | HEMA | 15 | 15 | 15 | — | 15 | 15 | 15 | 15 | 15 | 15 |
| Water | Distilled water | 40 | 40 | 40 | 40 | 40 | 40 | 40 | 40 | 40 | 40 |
| Polymerization initiator (g) | BAPO | 0.1 | 0.1 | 0.1 | 0.1 | 0.1 | 0.1 | 0.1 | 0.1 | 0.1 | 0.1 |
| | CQ | 0.2 | 0.2 | 0.2 | 0.2 | 0.2 | 0.2 | 0.2 | 0.2 | 0.2 | 0.2 |
| Polymerization accelerator (h) | DABE | 0.1 | 0.1 | 0.1 | 0.1 | 0.1 | 0.1 | 0.1 | 0.1 | 0.1 | 0.1 |
| | DEPT | 3 | 3 | 3 | 3 | 3 | 3 | 3 | 3 | 3 | 3 |
| Polymerization inhibitor | BHT | 0.05 | 0.05 | 0.05 | 0.05 | 0.05 | 0.05 | 0.05 | 0.05 | 0.05 | 0.05 |
| Tensile bond strength (MPa) | Without phosphoric acid etching (dentin) | Initial bond strength | 26 | 27 | 26 | 26 | 25 | 25 | 24 | 26 | 24 | 18 |
| | | Bond durability | 24 | 25 | 25 | 24 | 23 | 23 | 21 | 24 | 21 | 14 |
| | With phosphoric acid etching (dentin) | Initial bond strength | 28 | 30 | 30 | 27 | 29 | 28 | 27 | 28 | 27 | 17 |
| | | Bond durability | 25 | 27 | 28 | 25 | 26 | 26 | 23 | 24 | 24 | 9 |

TABLE 5

| Components | Content (parts by weight) |
|---|---|
| Bis-GMA | 40 |
| HEMA | 40 |
| NPGDMA | 20 |
| CQ | 0.6 |
| BAPO | 0.5 |
| DABE | 2 |
| R972 | 6 |
| Ar380 | 1.5 |

As shown in Table 4, the primers (Examples 2-1 to 2-9) as the dental adhesive according to the present invention exhibited an initial bond strength of 24 MPa or more, and a bond durability of 21 MPa or more to dentin, regardless of whether the dentin was treated or untreated by phosphoric acid etching. On the other hand, as shown in Table 4, the bonding material (Comparative Example 2-1) that contained the asymmetric acrylamide-methacrylic acid ester compound (b) of the present invention, and that contained the wherein the (meth)acrylamide compound (a) is at least one compound selected from the group consisting of compounds represented by the following general formula (1), and compounds represented by the following general formula (2), and
wherein the asymmetric acrylamide-methacrylic acid ester compound (b) is a compound represented by the following general formula (3),

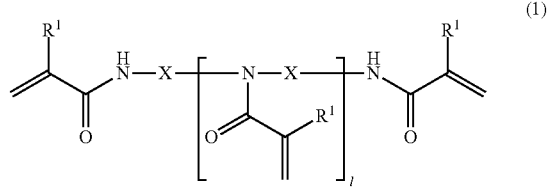

wherein $R^1$ represents a hydrogen atom or a methyl group, 1 represents an integer of 1 to 6, X represents an optionally substituted, linear or branched $C_1$ to $C_8$ alkylene group, the plurality of $R^1$ may be the same or different, and the plurality of X may be the same or different,

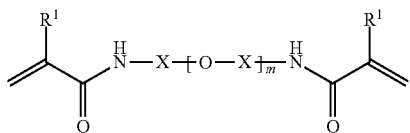

(2)

wherein m represents 2 or 3, $R^1$ and X are as defined above, the plurality of $R^1$ may be the same or different, and the plurality of X may be the same or different,

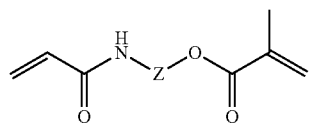

(3)

wherein Z is an optionally substituted, linear or branched $C_1$ to $C_8$ aliphatic group or an optionally substituted aromatic group, the aliphatic group being optionally interrupted by at least one linking group selected from the group consisting of —O—, —S—, —CO—, —CO—O—, —O—CO—, —NR²—, —CO—NR²—, —NR²—CO—, —CO—O—NR²—, —O—CONR²—, and —NR²—CO—NR²—, and $R^2$ represents a hydrogen atom, or an optionally substituted, linear or branched $C_1$ to $C_8$ aliphatic group.

2. The dental adhesive according to claim 1, further comprising a hydrophilic polymerizable monomer (d).

3. The dental adhesive according to claim 1, wherein the acid group-containing (meth)acrylic polymerizable monomer (c) is a phosphoric acid group-containing (meth)acrylic polymerizable monomer.

4. The dental adhesive according to claim 1, further comprising a hydrophobic crosslinkable polymerizable monomer (e).

5. The dental adhesive according to claim 2, wherein the hydrophilic polymerizable monomer (d) contains a monofunctional (meth)acrylamide compound (d-1) represented by the following general formula (4),

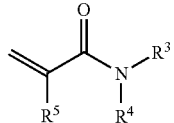

(4)

wherein $R^3$ and $R^4$ are each independently a $C_1$ to $C_3$ alkyl group, and $R^5$ is a hydrogen atom or a methyl group.

6. The dental adhesive according to claim 1, wherein the (meth)acrylamide compound (a) is at least one selected from the group consisting of the following compounds (a1-1), (a1-3), (a1-5), and (a1-7);

Compound (a1-1)
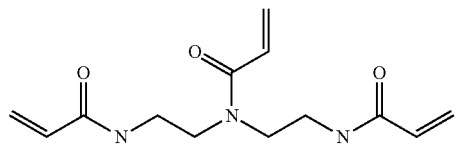

Compound (a1-3)
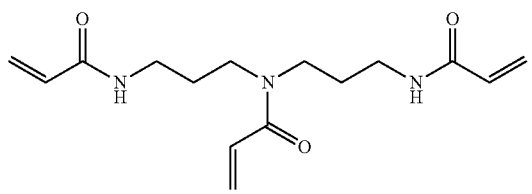

Compound (a1-5)
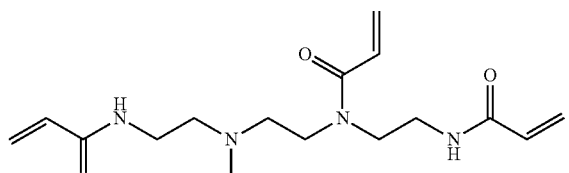

Compound (a1-7)
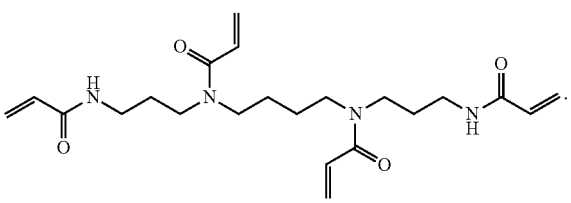

7. The dental adhesive according to claim 1, wherein the (meth)acrylamide compound (a) is at least one selected from the group consisting of the following compounds (a2-1), (a2-3), (a2-5), (a2-7), and (a2-21);

Compound (a2-1)
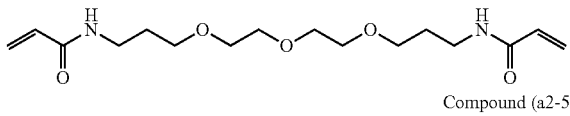

Compound (a2-5)
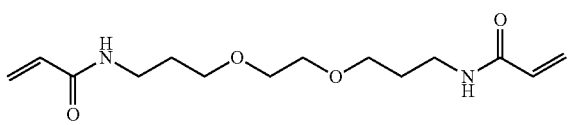

Compound (a2-3)
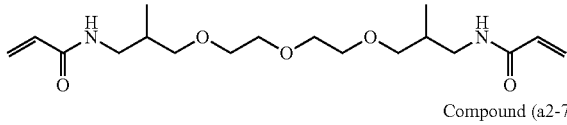

Compound (a2-7)
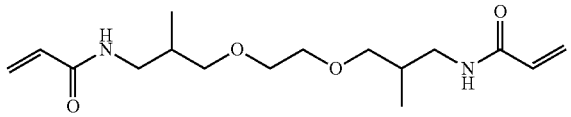

Compound (a2-21)

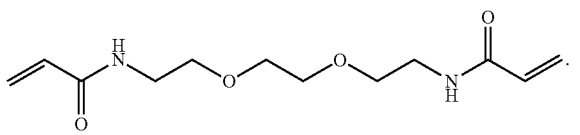

8. The dental adhesive according to claim 1, wherein the (meth)acrylamide compound (a) is the following compound (a2-1);

Compound (a2-1)

9. The dental adhesive according to claim 1, wherein the (meth)acrylamide compound (a) is the following compound (a2-21);

10. The dental adhesive according to claim 1, wherein the asymmetric acrylamide-methacrylic acid ester compound (b) is a compound represented by the general formula (3) in which Z is an optionally substituted, linear or branched $C_2$ to $C_4$ aliphatic group.

11. The dental adhesive according to claim 1, wherein the asymmetric acrylamide-methacrylic acid ester compound (b) is at least one selected from the group consisting of N-methacryloyloxyethylacrylamide, N-methacryloyloxypropylacrylamide, N-methacryloyloxybutylacrylamide, N-(1-ethyl-(2-methacryloyloxy)ethyl)acrylamide, and N-(2-(2-methacryloyloxyethoxy)ethyl)acrylamide).

* * * * *